United States Patent
Vassallo

(10) Patent No.: US 7,337,781 B2
(45) Date of Patent: Mar. 4, 2008

(54) IMPLANT FOR TONGUE

(75) Inventor: Charles Vassallo, Oxford, CT (US)

(73) Assignee: Restore Medical, Inc., St. Paul, MN (US)

( * ) Notice: Subject to any disclaimer, the term of this patent is extended or adjusted under 35 U.S.C. 154(b) by 210 days.

(21) Appl. No.: 11/107,160

(22) Filed: Apr. 15, 2005

(65) Prior Publication Data

US 2006/0235264 A1    Oct. 19, 2006

(51) Int. Cl.
*A61B 19/00*    (2006.01)
(52) U.S. Cl. ................................. 128/897; 128/848
(58) Field of Classification Search ........ 128/897–898, 128/846, 848, 859; 623/9, 11.11, 14.11; 602/902
See application file for complete search history.

(56) References Cited

U.S. PATENT DOCUMENTS

| | | | |
|---|---|---|---|
| 5,843,021 A | 12/1998 | Edwards et al. | |
| 5,988,171 A | 11/1999 | Sohn et al. | |
| 6,161,541 A | 12/2000 | Woodson | |
| 6,250,307 B1 | 6/2001 | Conrad et al. | |
| 6,431,174 B1 | 8/2002 | Knudson et al. | |
| 6,513,530 B2 | 2/2003 | Knudson et al. | |
| 6,523,542 B2 | 2/2003 | Knudson et al. | |
| 6,601,584 B2 | 8/2003 | Knudson et al. | |
| 2004/0139975 A1 | 7/2004 | Nelson et al. | |
| 2004/0149290 A1 | 8/2004 | Nelson et al. | |
| 2005/0092332 A1 | 5/2005 | Conrad et al. | |
| 2005/0092334 A1 | 5/2005 | Conrad et al. | |

FOREIGN PATENT DOCUMENTS

| | | |
|---|---|---|
| DE | 197 56 956 C1 | 7/1999 |
| DE | 199 20 114 A1 | 11/2000 |
| EP | 1 039 859 B1 | 12/2003 |
| WO | WO 2005/082452 A1 | 9/2005 |
| WO | WO 2006/072571 A1 | 7/2006 |

OTHER PUBLICATIONS

Ersek et al., "Minimally Invasive Macro Implants," *Worldplast*, vol. 1, No. 4, pp. 275-285 (1996).
Brochure, "EPI-Lasik Laser Course. Scandinavian Course on Laser Vision Correction Refractive Surgery," 4 pages (Jun. 9, 2005).
Eisele, D. et al., "Direct Hypoglossal Nerve Stimulation in Obstructive Sleep Apnea," *Arch Otolaryngol. Head Neck Surg.*, vol. 123, pp. 57-61 (Jan. 1997).
Miller, F. et al., "Role of the tongue base suspension suture with The Repose System bone screw in the multilevel surgical management of obstructive sleep apnea," *Otolaryngol. Head Neck Surg.*, vol. 126, No. 4, pp. 392-398 (Apr. 2002).

(Continued)

*Primary Examiner*—John P. Lacyk
(74) *Attorney, Agent, or Firm*—Merchant & Gould P.C.

(57) ABSTRACT

A method and apparatus for treating a condition of a patient's airway includes identifying a patient with obstructive sleep apnea and identifying a muscle of a tongue of the patient. A first brace is implanted within the tongue at a first implant location near the top of the tongue. A second brace is implanted within the tongue at a second implant location below the upper location. The first and second braces are connected to compress the muscle group.

13 Claims, 20 Drawing Sheets

OTHER PUBLICATIONS

Powell, N. et al., "Radiofrequency Volumetric Reduction of the Tongue—A Porcine Pilot Study for the Treatment of Obstructive Sleep Apnea Syndrome," *CHEST*, vol. 111, No. 5, pp. 1348-1355 (May 1997).

Powell, N. et al., "Radiofrequency tongue base reduction in sleep-disordered breathing: A pilot study," *Otolaryngol. Head Neck Surg.*, vol. 120, No. 6, pp. 656-664 (May 1999).

Thomas, A. et al., "Preliminary findings from a prospective, randomized trial of two tongue-base surgeries for sleep-disordered breathing," *Otolaryngol. Head Neck Surg.*, vol. 129, No. 5, pp. 539-546 (Nov. 2003).

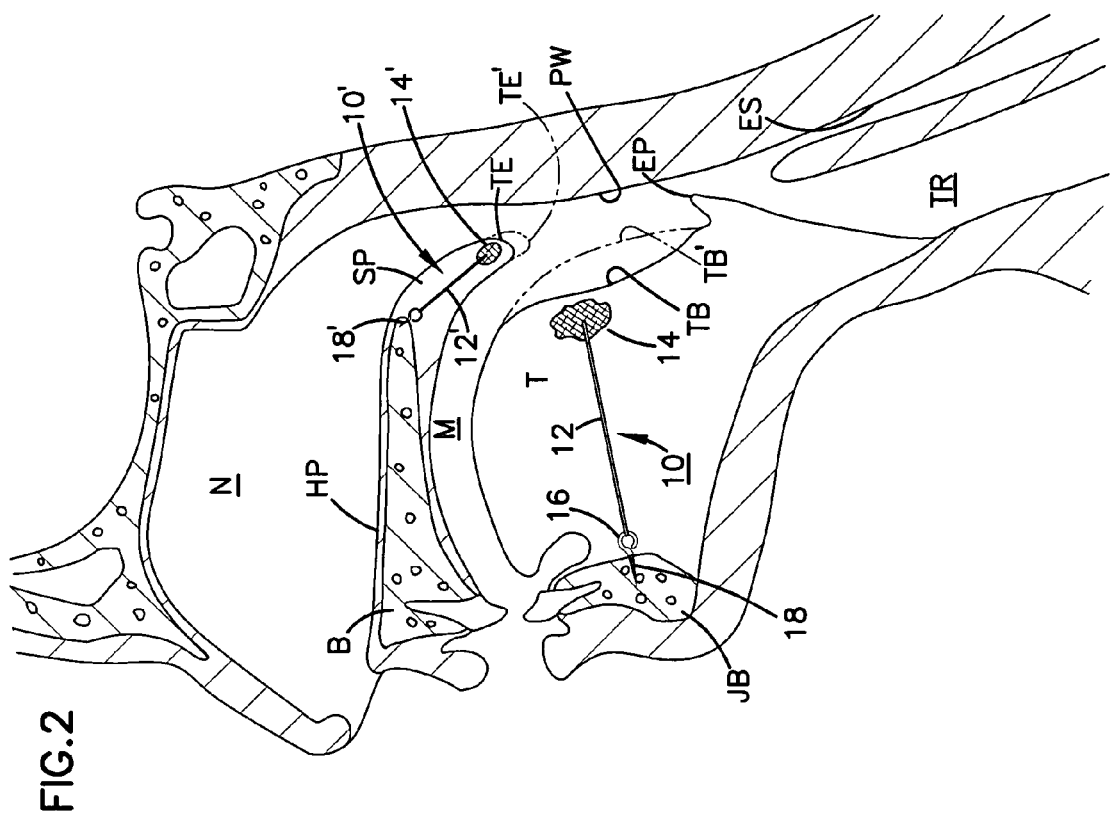
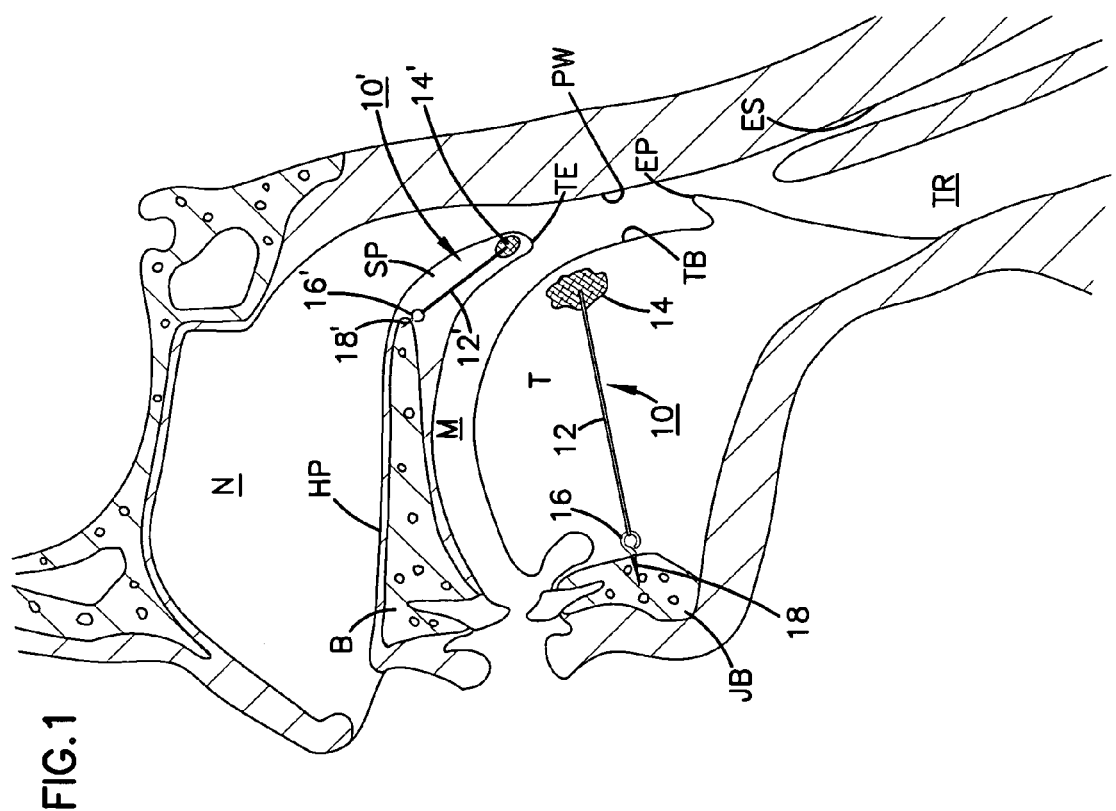

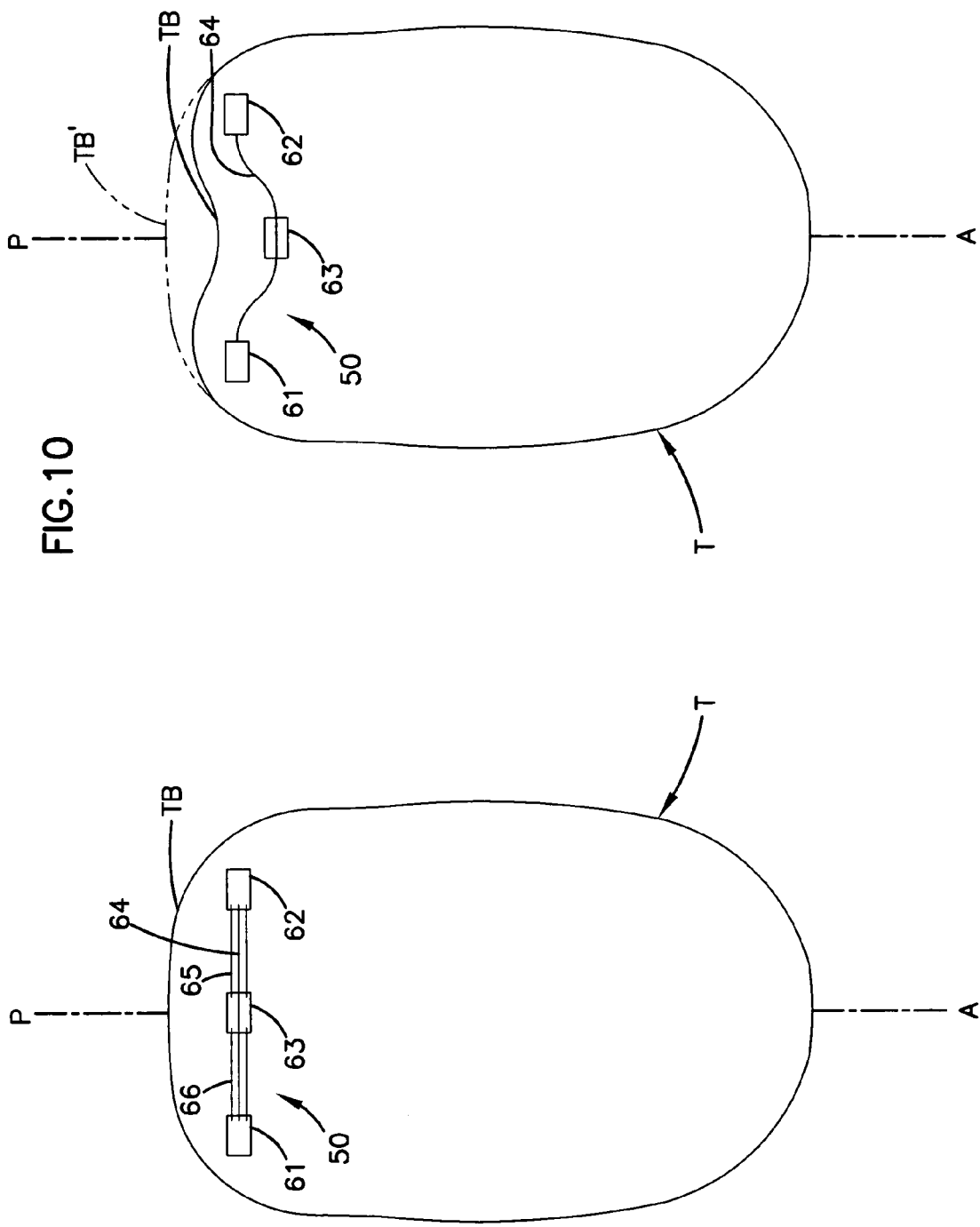

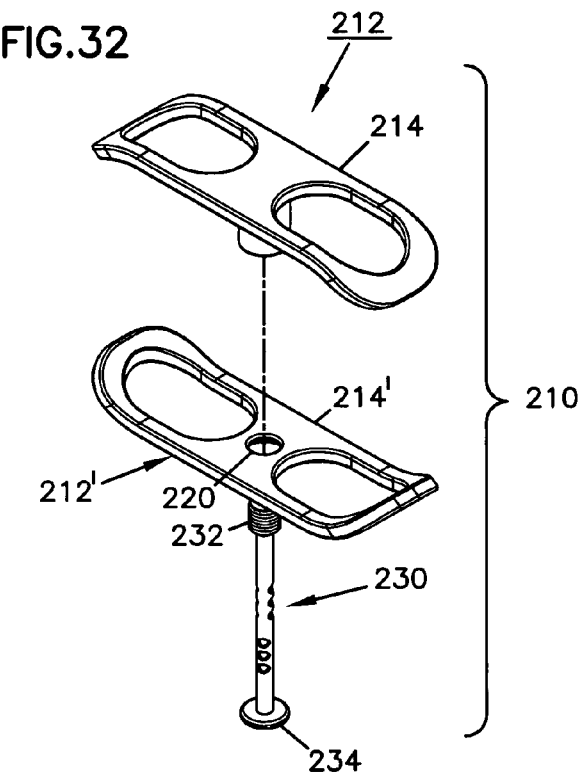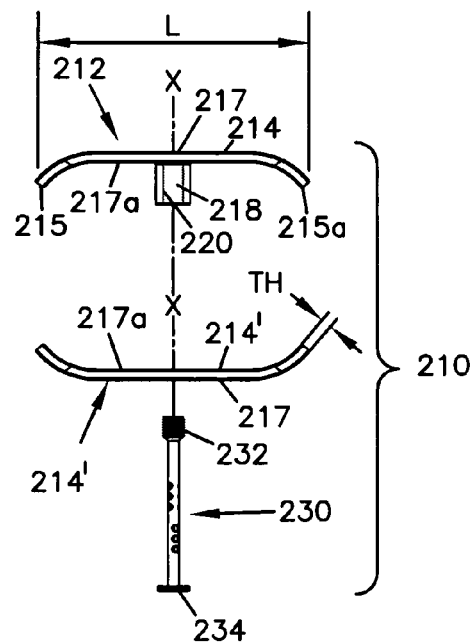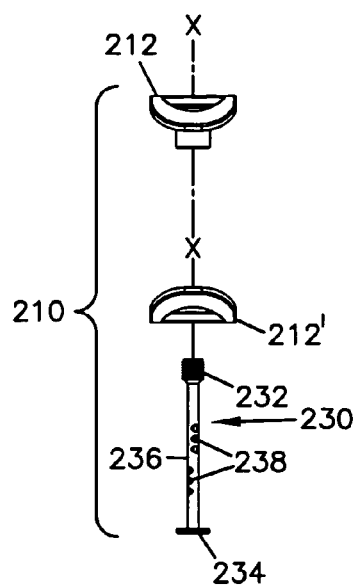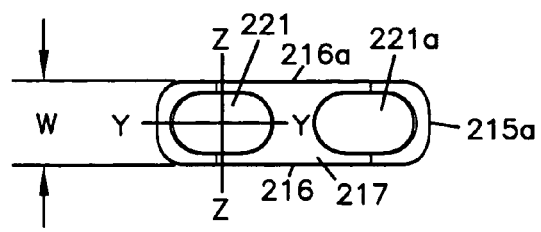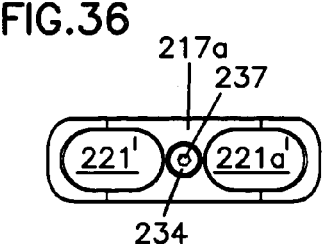

IMPLANT FOR TONGUE

BACKGROUND OF THE INVENTION

1. Field of the Invention

This invention pertains to a method and apparatus for treating a condition of an upper airway of a patient. More particularly, this invention is directed to such a method and apparatus including an implant to improve patency of the airway.

2. Description of the Prior Art

Upper airway conditions such as obstructive sleep apnea ("OSA") and snoring have received a great deal of attention. These conditions have recognized sociological and health implications for both the patient and the patient's bed partner.

Numerous attempts have been made towards treating OSA and snoring. These include placing implants in either the tissue of the soft palate or the pharyngeal airway as disclosed in commonly assigned U.S. Pat. No. 6,250,307 to Conrad et al. dated Jun. 26, 2003, U.S. Pat. No. 6,523,542 to Metzger et al. dated Feb. 25, 2003 and U.S. Pat. No. 6,431,174 to Knudson et al. dated Aug. 13, 2002. Further, U.S. Pat. No. 6,601,584 to Knudson et al. dated Aug. 5, 2003 teaches a contracting implant for placement in the soft palate of the patient.

In the '584 patent, an embodiment of the contracting implant includes two tissue attachment ends (for example ends 102b in FIGS. 46 and 47) which are maintained in a space-apart, stretched relation by a bio-resorbable member 102c which surrounds an internal spring or resilient member 102a. After implantation, tissue grows into the attachment ends 102b. The bioresorbable member 102c is selected to resorb after the tissue in-growth permitting the resilient member 102a to contract drawing ends 102b together as illustrated in FIG. 47 of the '584 patent (incorporated herein by reference). Tissue contraction is believed to be desirable in that the tissue contraction results in a debulking of the tissue and movement of tissue away from opposing tissue surfaces in the pharyngeal upper airway.

Another prior art technique for treating OSA or snoring is disclosed in U.S. Pat. No. 5,988,171 to Sohn et al. dated Nov. 23, 1999. In the '171 patent, a cord (e.g., a suture material) (element 32 in FIG. 6 of the '171 patent) is placed surrounding a base of the tongue and secured to the jaw by reason at an attachment member (element 20 in FIG. 6 of the '171 patent). In the method of the '171 patent, the member 32 can be shortened to draw the base of the tongue toward the jaw and thereby move the tissue of the base of the tongue away from the opposing tissue of the pharyngeal airway. However, this procedure is often uncomfortable. This procedure, referred to as tongue suspension, is also described in Miller et al., "Role of the tongue base suspension suture with The Repose System bone screw in the multilevel surgical management of obstructive sleep apnea", *Otolaryngol. Head Neck Surg.*, Vol. 126, pp. 392-398 (2002).

Two tongue-based surgeries are compared in Thomas et al., "Preliminary Finding from a Prospective, Randomized Trial of Two Tongue-Based Surgeries for Sleep Disordered Breathing", *Otolaryngology-Head and Neck Surg.*, Vol. 129, No. 5, pp. 539-546 (2003). This article compares tongue suspension (as described above) to tongue advancement (mandibular osteotomy).

Another technique for debulking tissue includes applying radio frequency ablation to either the tongue base or of the soft palate to debulk the tissue of the tongue or palate, respectively. This technique is illustrated in U.S. Pat. No. 5,843,021 to Edwards et al. dated Dec. 1, 1998. RF tongue base reduction procedures are described in Powell et al., "Radiofrequency tongue base reduction in sleep-disordered breathing: A pilot study", *Otolaryngol. Head Neck Surg.*, Vol. 120, pp. 656-664 (1999) and Powell et al., "Radiofrequency Volumetric Reduction of the Tongue—A Porcine Pilot Study for the Treatment of Obstructive Sleep Apnea Syndrome", *Chest*, Vol. 111, pp. 1348-1355 (1997).

A surgical hyoid expansion to treat OSA is disclosed in U.S. Pat. No. 6,161,541 to Woodson dated Dec. 19, 2000. Other tongue treatments for OSA include stimulation of the hypoglossal nerve. This procedure is described in Eisle et al., "Direct Hypoglossal Nerve Stimulation in Obstructive Sleep Apnea", *Arch. Otolaryngol. Head Neck Surg.*, Vol. 123, pp. 57-61 (1997).

U.S. patent application publication No. US 2004/0139975 published Jul. 22, 2004 and U.S. patent application publication No. US 2004/0149290 published Aug. 5, 2004 (both assigned to Apneon, Inc.) describe various implants for treating obstructive sleep apnea. In addition to describing implants for the soft palate and the pharyngeal wall, these applications describe implants for placement in the tongue. European patent application EPO 1039859 describes an implant in the tongue.

SUMMARY OF THE INVENTION

According to a preferred embodiment to the present invention, a method and apparatus are disclosed for treating a condition of a patient's airway. The method includes identifying a patient with obstructive sleep apnea and identifying a muscle of a tongue of the patient. A first brace is implanted within the tongue at a first implant location near the top of the tongue. A second brace is implanted within the tongue at a second implant location below the upper location. The first and second braces are connected to compress the muscle group.

BRIEF DESCRIPTION OF THE DRAWINGS

FIG. 1 is a side elevation, schematic view of a patient illustrating structure defining an upper airway of the patient and showing an implant according to an embodiment of the present invention positioned within the soft palate and secured to the bony structure of a hard palate and showing a similar implant in the tongue and secured to the bony structure of the jaw;

FIG. 2 is the view of FIG. 1 following contracting of the implants in the palate and tongue;

FIG. 9 is a view similar to FIG. 7 showing immediate post-implant of a still further embodiment of the present invention;

FIG. 10 is the view of FIG. 9 following tissue in-growth and resorption of bioresorbable elements;

FIG. 32 is a top, front and end, exploded perspective view of the muscle compression apparatus of FIG. 31;

FIG. 33 is a front elevation exploded view of the muscle compression apparatus of FIG. 32;

FIG. 34 is an end elevation exploded view of the muscle compression apparatus of FIG. 32;

FIG. 35 is a top plan view of the muscle compression apparatus of FIG. 32;

FIG. 36 is a bottom plan view of the muscle compression apparatus of FIG. 32;

DESCRIPTION OF THE PREFERRED EMBODIMENT

Figure 3:
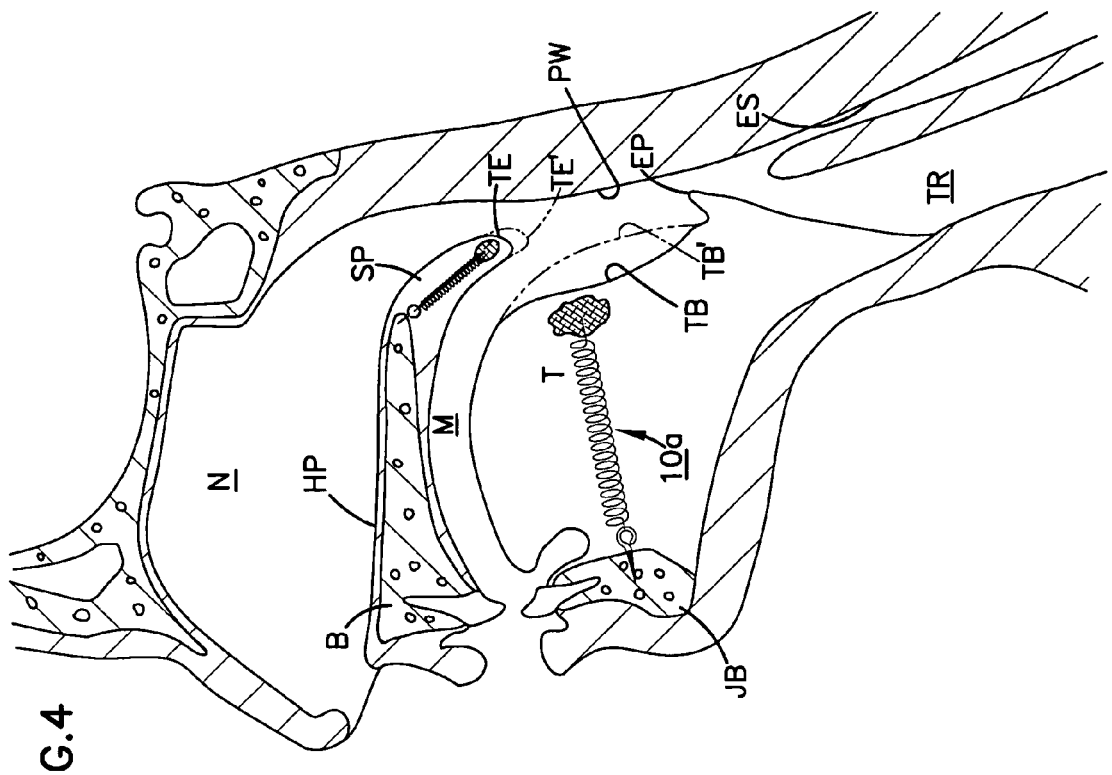
FIG. 3 is a view similar to that of FIG. 1 and showing an alternative embodiment of the present invention with implants of the alternative embodiment implanted in both the soft palate and tongue.

With reference now to the various drawing figures in which identical elements are numbered identically throughout, a description of the preferred embodiment of the present invention will now be provided. To facilitate a description and an understanding of the present invention, the aforementioned U.S. Pat. Nos. 6,250,307; 6,523,542; 6,431,174; 6,601,584; 5,988,171 and 5,843,021 are hereby incorporated herein by reference.

The assignee of the present application is assignee of co-pending U.S. patent application Ser. No. 10/877,003 filed Jun. 24, 2004 and Ser. No. 10/698,819 filed Oct. 31, 2003 and both entitled "Airway Implant". To facilitate an understanding of the present invention, a discussion of the disclosure of those two applications is first provided.

A. Disclosure of Parent Applications

1. U.S. patent application Ser. No. 10/698,819

The following is the disclosure of U.S. patent application Ser. No. 10/698,819 filed Oct. 31, 2003 with additional remarks:

With initial reference to FIG. 1, a soft palate SP is shown in side elevation view extending from a bony portion of a hard palate HP. The soft palate SP extends rearward to a trailing end TE. FIG. 1 also illustrates a tongue T with a base TB opposing a pharyngeal wall PW. A jawbone JB is shown at the lower front of the tongue T.

As a first described embodiment of the present invention, an implant 10 is shown in FIG. 1 completely implanted within the tongue T. A similar implant 10' is fully implanted in the soft palate SP. As will be apparent, implants 10, 10' are functionally and structurally similar differing only in size to facilitate placement in the tongue T and soft palate SP, respectively. As a result, a description of implant 10 will suffice as a description of implant 10' (with similar elements similarly numbered with the addition of an apostrophe to distinguish the implants 10, 10'). Further, while both implants 10, 10' are shown implanted in the same patient, either could be separately implanted.

The implant 10 includes an elongated member 12 having a tissue in-growth end 14 and a static end 16. The tissue in-growth end 14 may be any tissue growth inducing material (e.g., felt or PET) to induce growth of tissue into the end 14 to secure the end 14 to surrounding tissue following implantation. The elongated member 12 may be suture material one end secured to the felt 14 and with the static end 16 being a free end of the suture material 12.

An anchor 18 (shown in the form of a treaded eye-bolt although other fastening mechanisms could be used) is secured to the jawbone JB. In the case of implant 10', the anchor 18' is secured to the bone of the hard palate. The end 16 is secured to the anchor 18.

The end 14 is placed in the tongue near the tongue base TB. A surgeon adjusts a tension of the suture 12. This causes the tongue base TB to be urged toward the jawbone JB thereby placing the tissue of the tongue in compression. When a desired tension is attained, the surgeon may tie off the static end 16 at the bolt 18 retaining the tissue of the tongue T under tension. This method and apparatus provides a resistance to movement of the tongue base TB toward the pharyngeal wall PW. Similarly, with implant 10', the trailing end TE of the soft palate SP is urged away from the back of the throat and the soft palate SP is prevented from lengthening.

In the foregoing as well as all other embodiments in this application, one member 14 is shown. It will be appreciated that multiple member could be placed in the tongue T.

The embodiments of the present application show an anchor placed in the front center of the jawbone JB. It will be appreciated in this and all other embodiments, the anchor can be placed in other locations (for example, two anchors can be placed on opposite sides of the jaw bone with separate elongated members (e.g., elements 12, 10a, 172, 190 or 190' in the various figures) extending from each anchor.

Placing the implants 10, 10' under tension as in FIG. 1 provides therapy in that the tongue base TB and soft palate trailing end TE are retained from movement toward the pharyngeal wall PW. In addition, at time of initial implantation or thereafter, a surgeon may obtain access to anchors 18, 18' and further shorten the length of the elongated member 12 (i.e., by pulling the member 12 through the bolt 18, 18') to draw the tongue base or trailing end away from the pharyngeal wall to a new profile. This is illustrated in FIG. 2 with the contracted profile shown in solid lines TB, TE and contrasted with the original profile shown in phantom lines TB', TE'.

Figure 4:
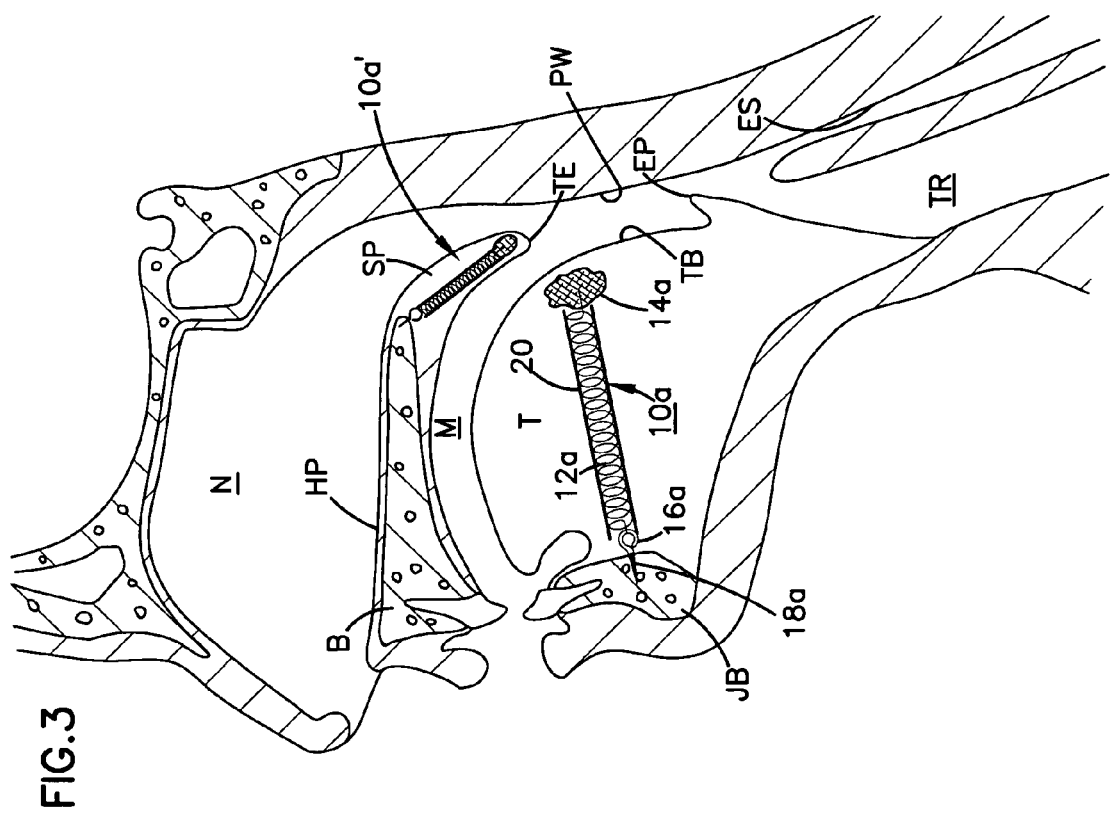
FIG. 4 is the view of FIG. 3 showing the implants in a contracted state.

Referring to FIGS. 3 and 4, an alternative embodiment of the present invention is shown as an implant 10a for the tongue T or implant 10a' for the soft palate SP. As with the embodiments of FIGS. 1 and 2, implants 10a, 10a' are functionally and structurally similar differing only in size to facilitate placement in the tongue and soft palate, respectively. As a result, a description of implant 10a will suffice as a description of implant 10a' (with similar elements similarly numbered with the addition of an apostrophe to distinguish the implants 10a, 10a'). Further, both implants 10a, 10a' are shown implanted in the same patient. Either or both implants could be implanted.

Implant 10a includes a tissue engaging end 14a and static end 16a. As in the embodiment of FIG. 1, the static end 16a is secured to a hard palate at the eyelet of an eyebolt 18a secured to the jawbone JB. Again, as in the embodiment of FIG. 1, the tissue-engaging end 14a may be any material which encourages tissue in-growth and attachment to tissue. An example of such a material may be PET or a felt material.

The tissue engaging end 14a and the static end 16a are connected by a resilient elongated member 12a which may be in the form of a spring member such as nitinol or other member which may be stretched to create a bias urging ends 14a, 16a toward one another. Opposing the bias of the spring member 12a is a bioresorbable material 20 positioned between the tissue-engaging end 14a and the bolt 18a.

After placement of the implant 10a within the tissue of the tongue and with the end 14a near the tongue base TB, the bio-resorbable material 20 will later resorb into the tissue of the tongue T permitting end 14a to be urged toward bolt 18a by the resilience of the spring 12a. This is illustrated in FIG. 4, where the contracted implant 10a places the tissue of the tongue under tension and urging the tongue base TB away from the pharyngeal wall PW. In FIG. 4, the contracted profile of the tongue base TB (and soft palate trailing end TE) is shown in solid lines and the original profile TB' (TE') is shown in phantom lines. Normal function of the tongue T is not impaired since the muscles of the tongue T can overcome the bias of the spring member 12a.

Figure 5:
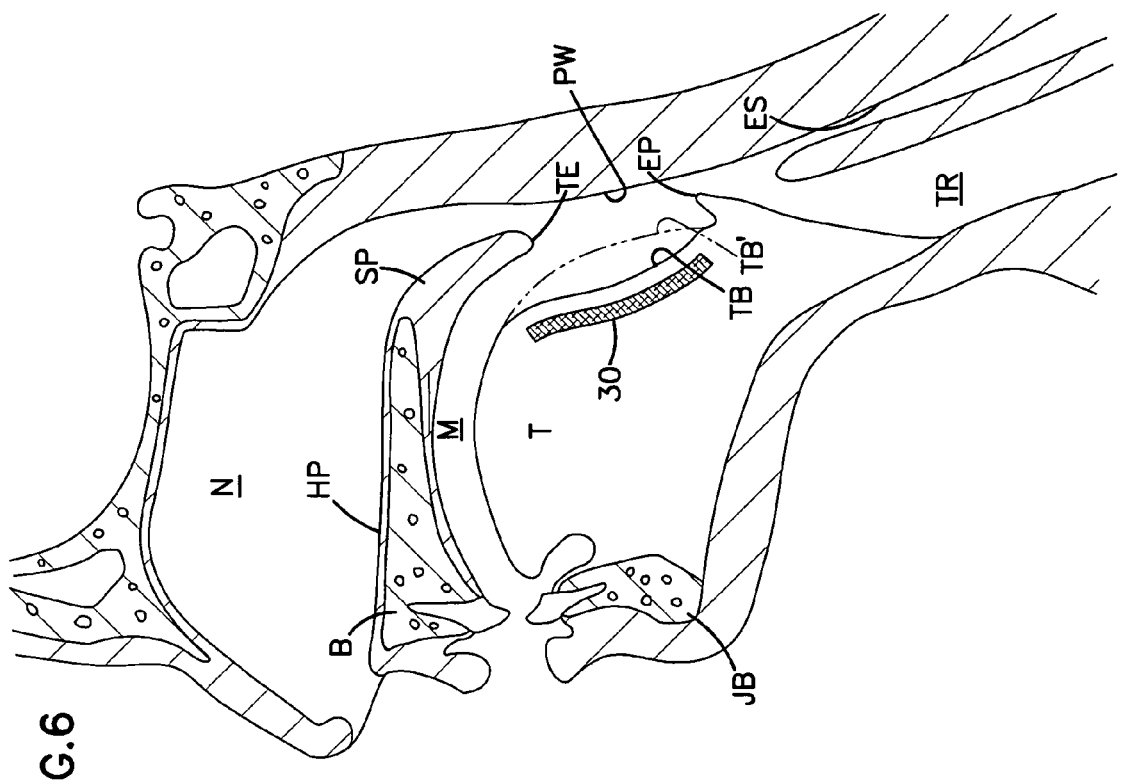
FIG. 5 is a view similar to that of FIG. 1 and showing a further alternative embodiment of the present invention with an implant of the further alternative embodiment implanted in the tongue.
Figure 6:
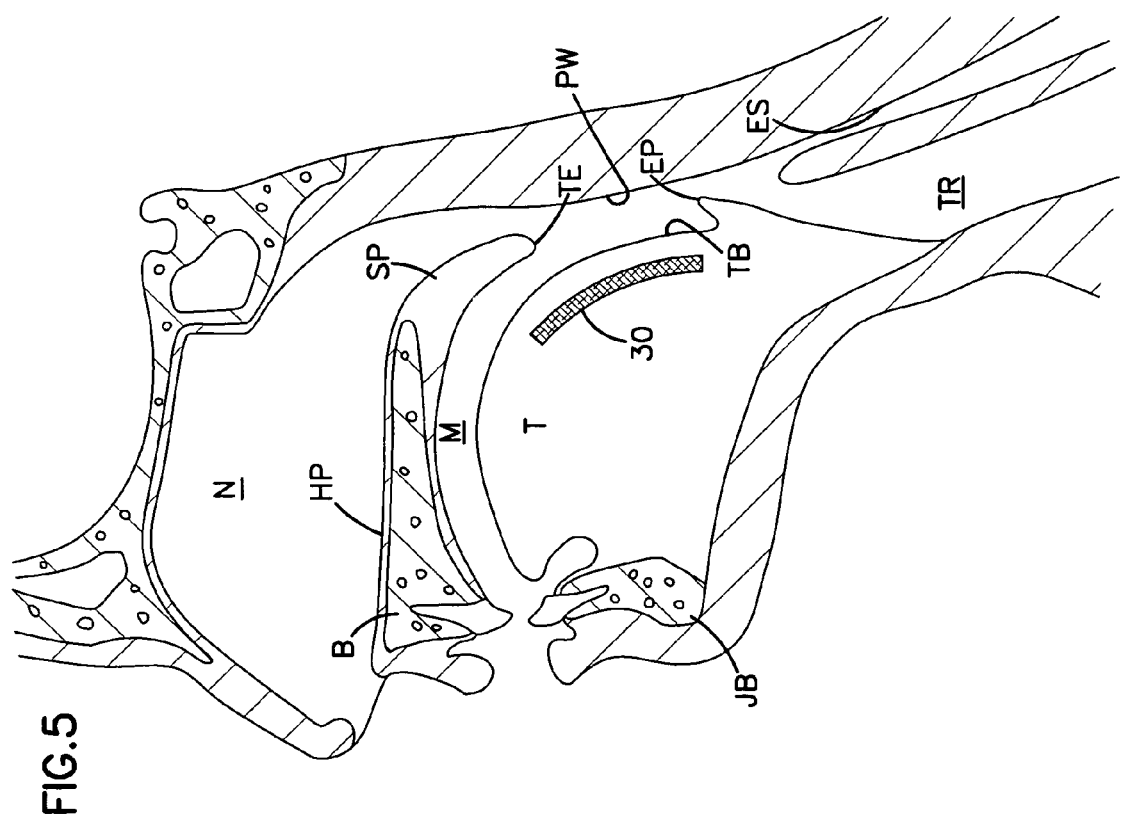
FIG. 6 is the view of FIG. 5 contraction of tissue around the implant.
Figure 7:
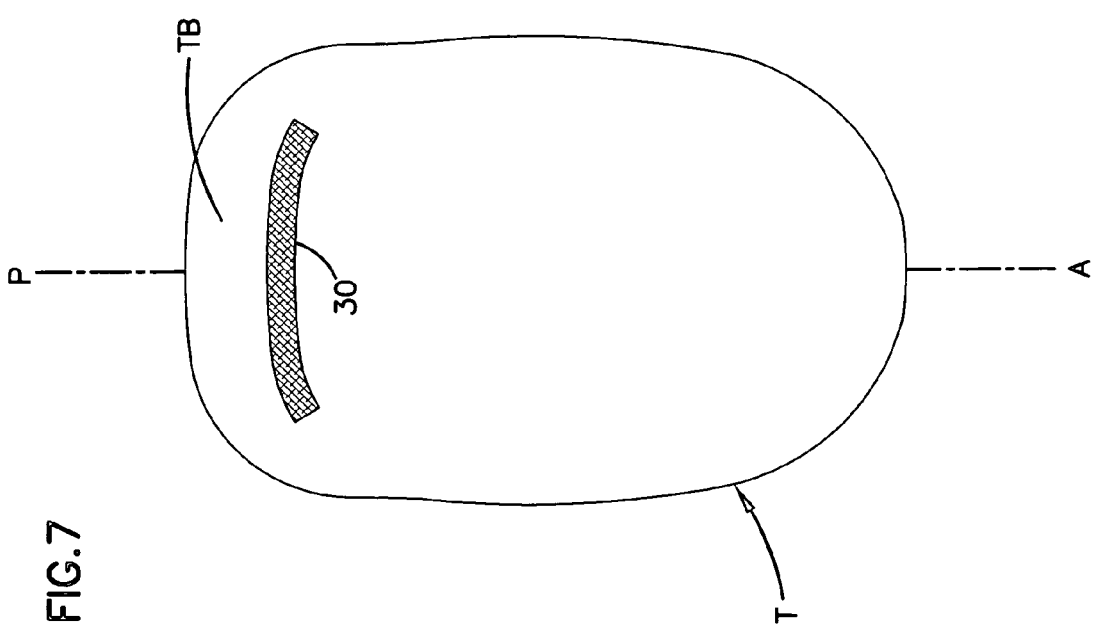
FIG. 7 is a top plan view of FIG. 5 showing an anterior-posterior axis A-P of the tongue.

FIGS. 5-7 illustrate a still further embodiment for reducing the tongue base TB. While term "reducing" is used, it will be appreciated in this and other embodiments that the tongue need not be reduced in volume but can be reshaped are simply displaced by the disclosed inventions to achieve the desired effect. In this embodiment, a sheet 30 of tissue in-growth material (e.g., a sheet of felt with numerous interstitial space) is place in the tongue near the base TB. The sheet 30 is placed beneath the tongue surface and parallel to the base TB substantially covering the area of the tongue base TB. Scarring from the material contracts over time resulting in a reduction in the tongue base as illustrated in FIG. 6. To heighten the amount of tongue base reduction, the sheet 30 may be impregnated with a tissue reducing or stiffening agent (e.g., a sclerosing agent).

FIGS. 9 and 10 illustrate a further variant of FIGS. 5-7. The implant 50 includes three tissue in-growth pads 61, 62, 63. A nitinol bar 64 connects the pads 61-63 in-line with pad 63 centrally positioned. The bar 64 is pre-stressed to have a central bend shown in FIG. 10. Bio-resorbable sleeves 65, 66 hold the bar 64 in a straight line against the bias of bar 64 as in FIG. 9. The implant 50 is implanted as shown in FIG. 9 with the straight bar 64 parallel to the tongue base TB. After implantation, tissue grows into pads 61-63. After the time period of in-growth, the sleeves resorb as in FIG. 10. With the sleeves resorbed, the bar 64 bends to its pre-stressed shape. The tongue base moves with the pad 63 to reposition the tongue base (illustrated in FIG. 10 as the shift from TB' to TB).

Figure 8:
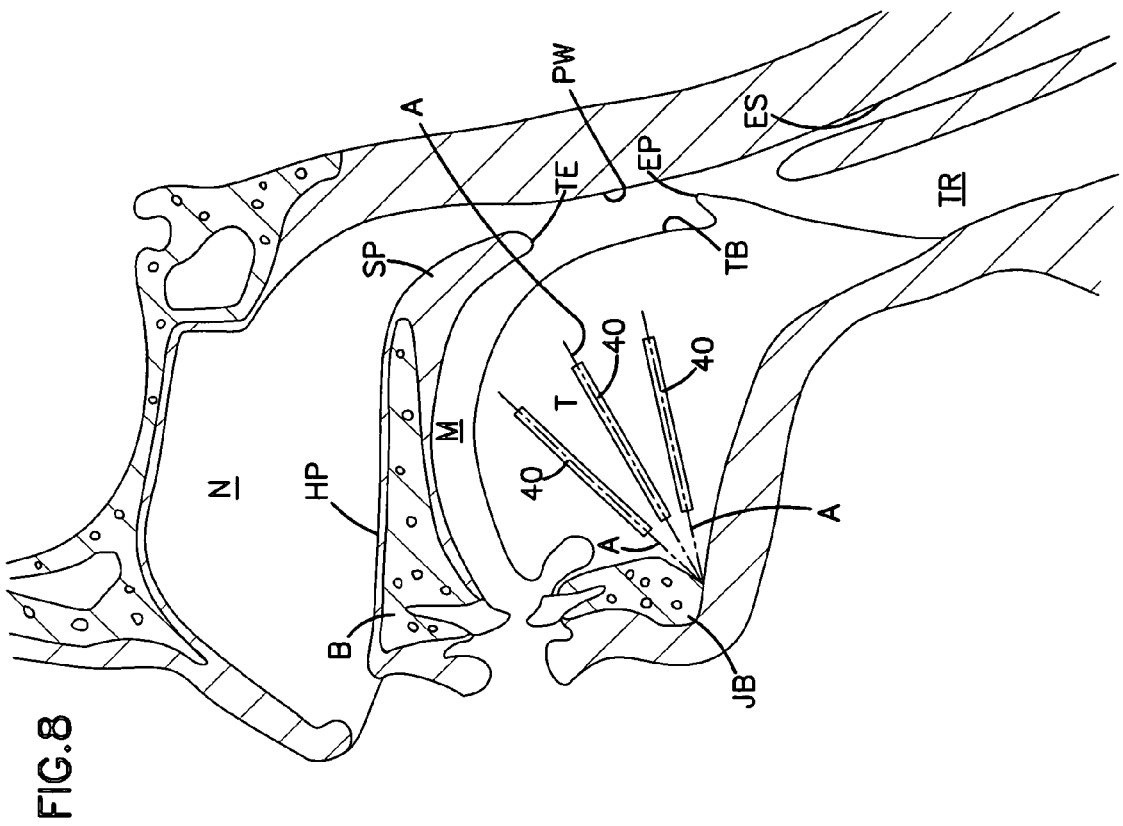
FIG. 8 is a view similar to that of FIG. 1 and showing a yet further alternative embodiment of the present invention with an implants of the yet further alternative embodiment implanted in the tongue.

FIG. 8 illustrates a still further embodiment of the invention for reducing the tongue base. Certain muscles of the tongue (particularly, the genioglossus muscles) radiate from the jawbone JB to the tongue surface as illustrated by lines A in FIG. 8. Contracting implants 40 identical to those in FIGS. 46 and 47 of U.S. Pat. No. 6,601,584 are placed with a contracting axis (the axis between tissue in-growth ends 14a'—identical to ends 102b in FIGS. 46, 47 of the '584 patent) are placed in the tongue in-line with the muscle radiating lines A. Alternatively, the contracting implant 40 may be of the construction shown in FIGS. 48 and 49 of the '584 patent. As the implants contract over time, they urge the tongue from collapsing toward the pharyngeal wall. In lieu of contracting implants, the elongated implants can be static implants such as implants shown in FIG. 11 of U.S. Pat. No. 6,250,307 and labeled 20.

2. U.S. patent application Ser. No. 10/698,819

Figure 11:
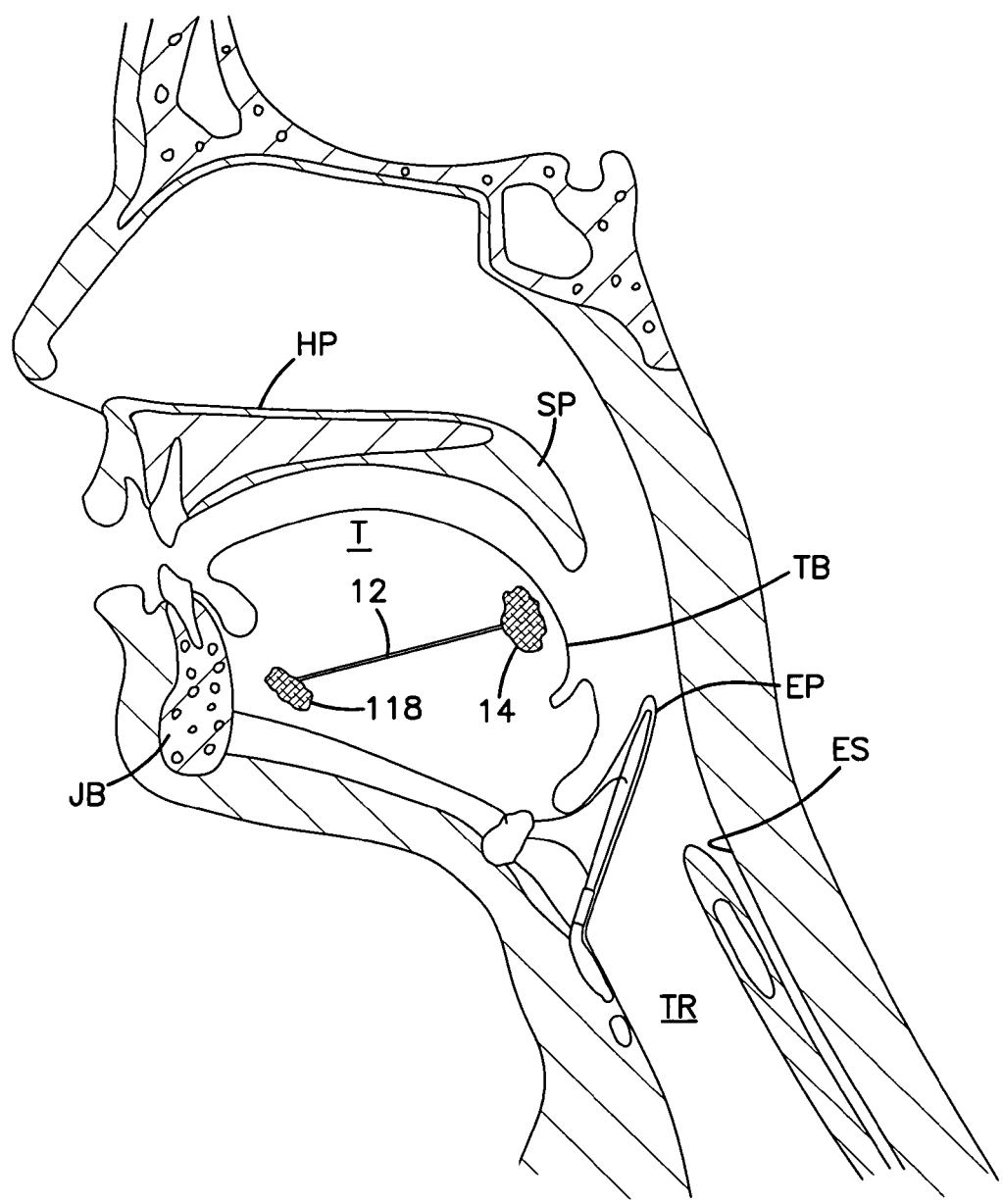
FIG. 11 is a view similar to that of FIGS. 1 and 2 showing an alternative embodiment.

The following is the disclosure of U.S. patent application Ser. No. 10/698,819 filed Oct. 31, 2003:

FIG. 11 is a view similar to that of FIGS. 1 and 2 showing an alternative embodiment. Elements in common with those of FIGS. 1 and 2 are numbered identically. The tissue in-growth end 14 is embedded in the tongue T near the tongue base TB. In stead of an anchor 18 in the jaw bone JB as described with reference to FIG. 1, the embodiment of FIG. 11 employs and additional tissue in-growth material 118 embedded in the tongue T near the jaw bone JB. An elongated member 12 (e.g., suture material) acts as a tension member and connects the base tissue in-growth member 14 to the jawbone tissue in-growth member 118. As in the embodiment of FIG. 1, the surgeon can adjust the tension on suture 12. Alternatively, the suture 12 can be replaced with the elements 12a and 20 of FIG. 3.

The tissue in-growth material 118 acts as an embedded anchor and eliminates the need for placement of an anchor 18 in the jawbone JB as described in previous embodiments.

Figure 12:
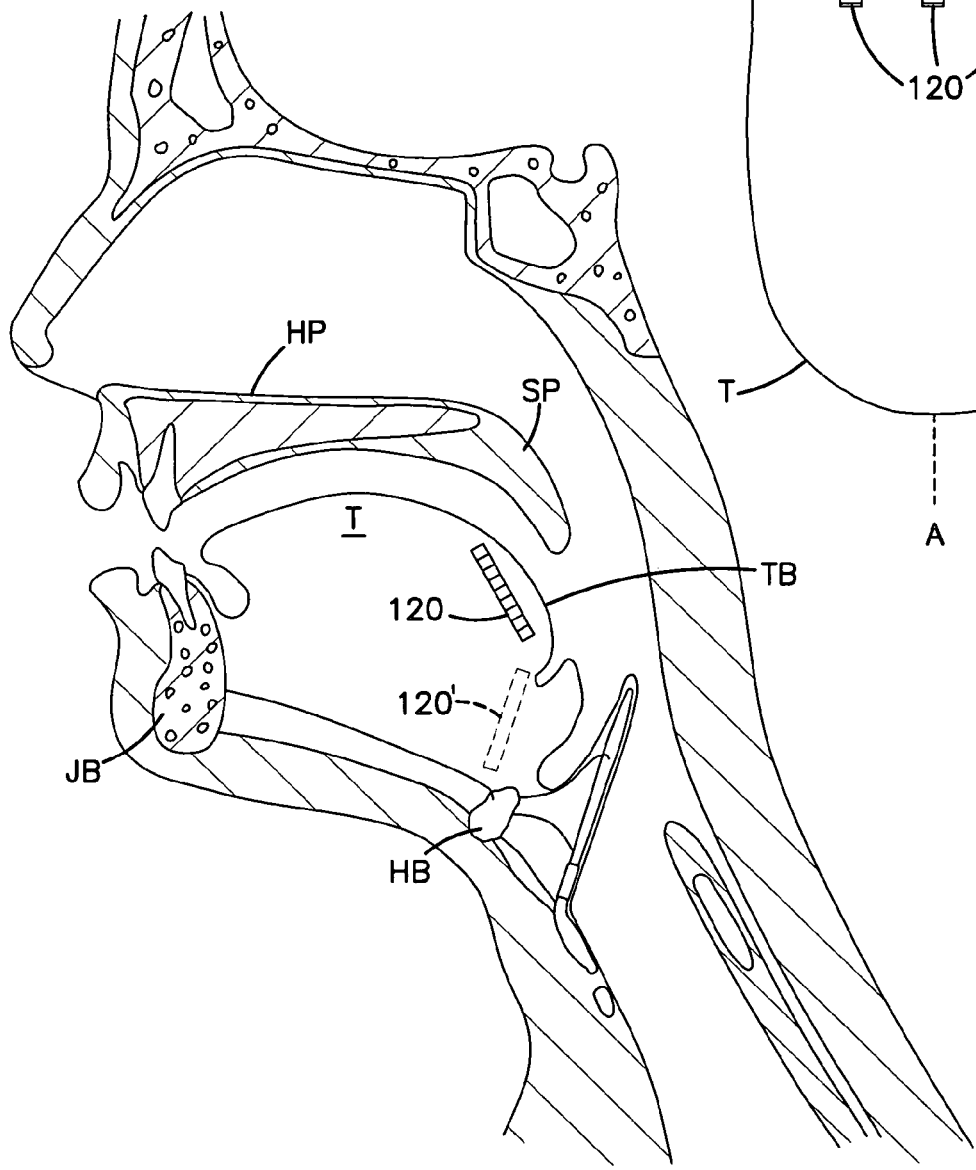
FIG. 12 is the view of FIG. 11 showing a further alternative embodiment of the invention.
Figure 13:
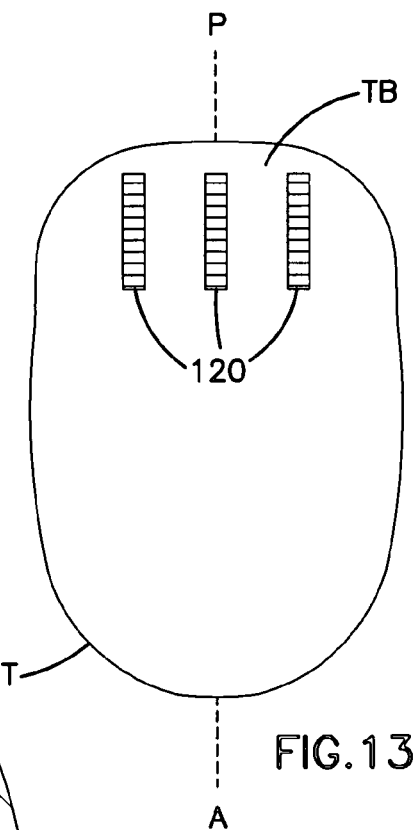
FIG. 13 is a top plan view of the tongue of FIG. 12 and shown with reference to an anterior-posterior axis A-P.

FIGS. 12 and 13 show placement of implants 120 in the tongue T near the base TB. Three implants 120 are shown in parallel alignment near the base TB and extending generally parallel to the wall of the tongue base TB. The implants may be polyester braids such as those described in U.S. Pat. No. 6,513,530 to Brenzel et al. dated Feb. 4, 2003 or may be contracting implants such as those described with reference to FIG. 8. The implants 120 tend to stiffen the base of the tongue and resist floppy action or lack of tone in the tissue of the tongue T near the base TB. The implants 120 are spaced apart for fibrosis to interconnect between the implants 120. In FIG. 12, an alternative placement of the implant 120 is shown and illustrated in phantom lines as implant 120'. Implant 120' is positioned near the tongue base TB with one end near the hyoid bone HB and extending upwardly therefrom.

Figures 14, 15:
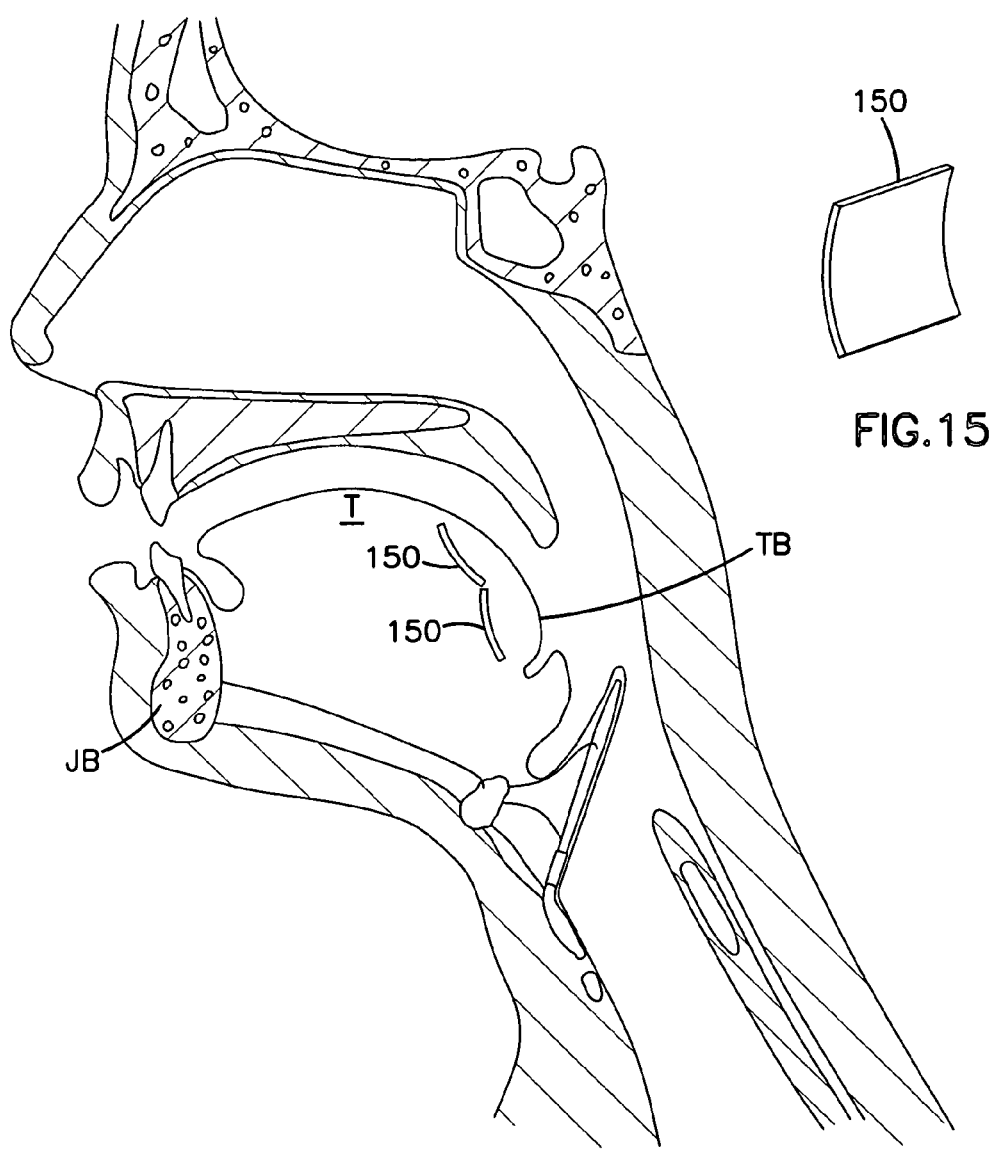
FIG. 14 is the view of FIG. 11 showing a further alternative embodiment of the invention with crimps shown in the tongue in an un-crimped state.
FIG. 15 is a perspective view of the crimp in the state of FIG. 14.
Figure 16:
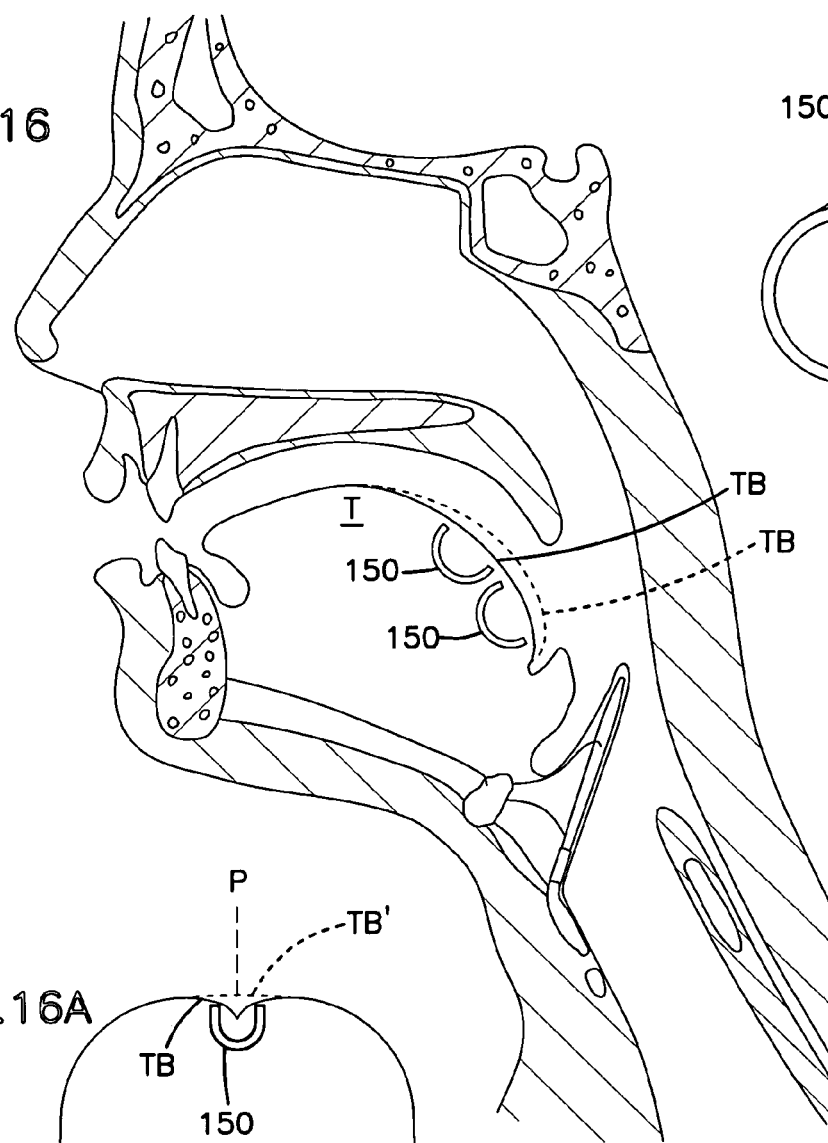
FIG. 16 is the view of FIG. 14 showing the crimps in a crimped state.
Figure 17:
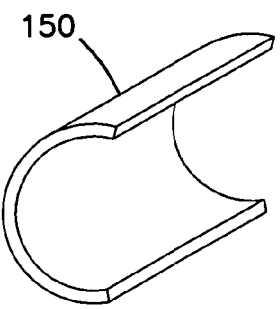
FIG. 17 is a perspective view of the crimp in the state of FIG. 16.
Figure 16A:
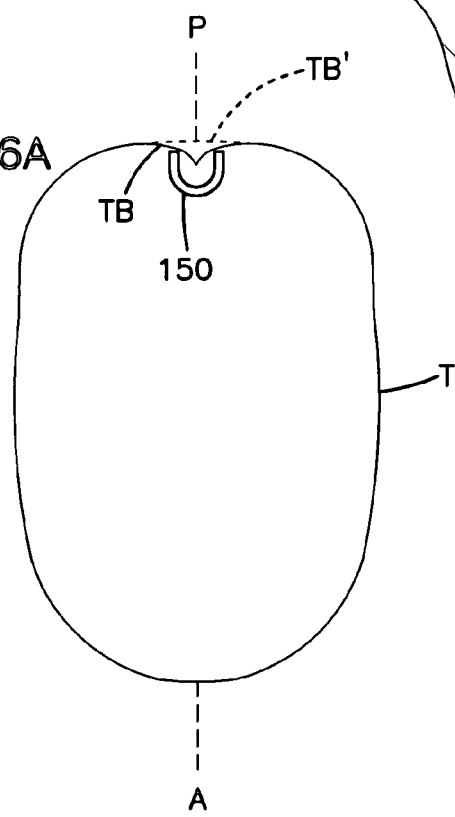
FIG. 16A is a top plan view of a tongue showing an anterior-posterior axis (A-P) and illustrating and alternative orientation of the crimp of FIGS. 14-16.

FIGS. 14-17 illustrate the use of imbedded crimps (or staples) to stiffen and potentially reshape the tongue base TB. As illustrated in FIGS. 14 and 15 the crimps 150 are slightly curved members with are placed in the tongue T with concave surfaces opposing the tongue base TB. The crimps 150 are crimped by in situ to a crimped U-shape. The crimping acting squeezes tissue of the tongue to stiffen the tongue. Crimping can also reshape the tongue base TB as illustrated in FIG. 16 (phantom lines illustrating the pre-crimped shape of the tongue base TB). The crimps 150 may be any biocompatible material which plastically deforms to a crimped state. FIG. 16A shows an alternative orientation of the crimp or staples 150. The crimp 150 is rotated 180 degrees from the orientation of FIG. 16 with the crimp 150 at the center of the tongue based TB to result in a crimped in center of the tongue from the original tongue base TB profile shown in phantom lines in FIG. 16A.

Figure 18:
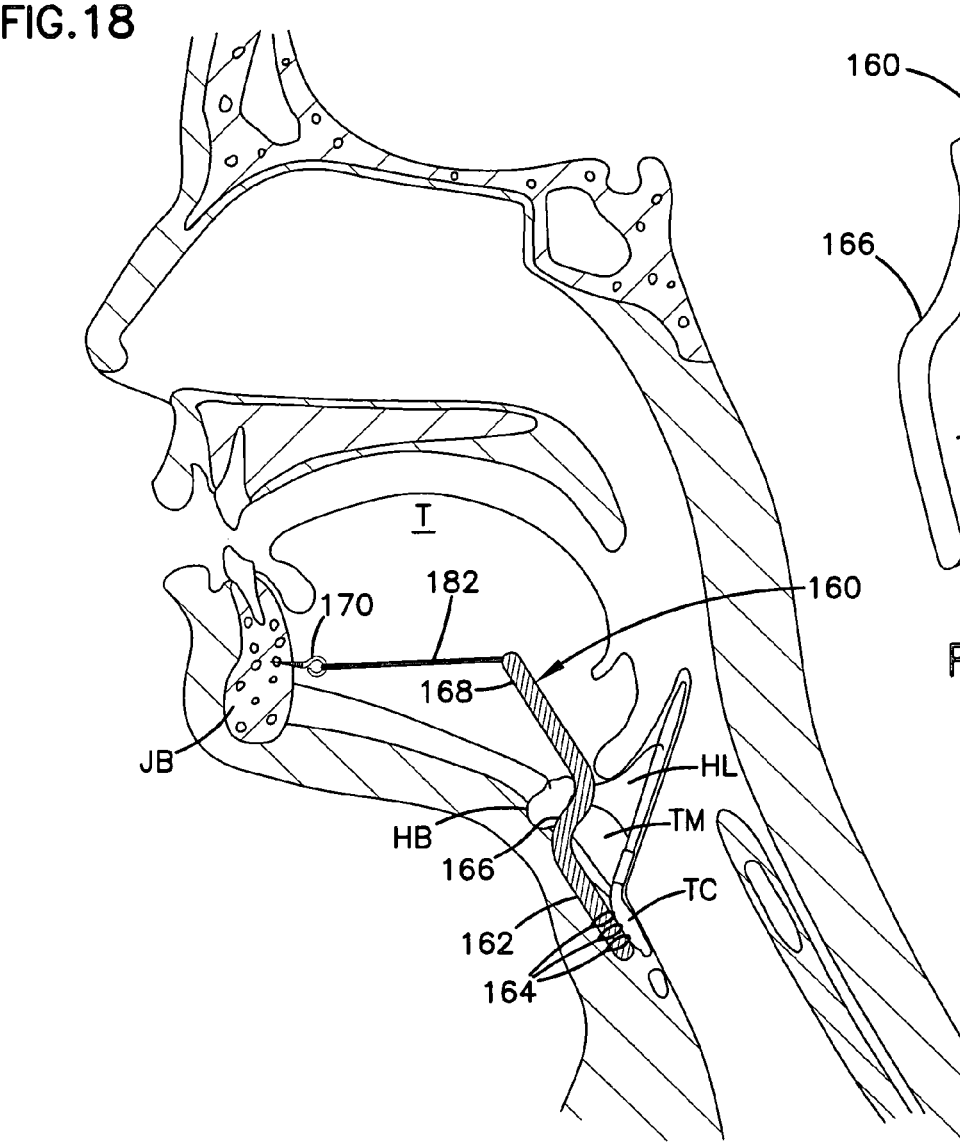
FIG. 18 is the view of FIG. 11 showing a further alternative embodiment of the invention with a lever positioned to advance a hyoid bone of a patient.
Figure 19:
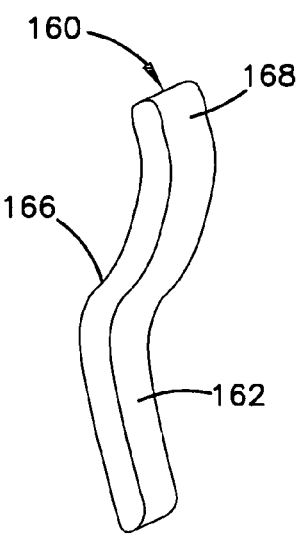
FIG. 19 is a perspective view of the lever of FIG. 18.

FIGS. 18 and 19 illustrate an embodiment to advance the hyoid bone (HB). In FIGS. 18 and 19 and lever 160 is provided with a first end 162 adapted to be placed against an anterior surface of thyroid cartilage TC. The end 162 is secured to the thyroid cartilage TC by any suitable means (e.g., sutures 164 or staples or bio-adhesives).

The lever 160 is bent to present an abutting surface 166 which abuts a posterior surface of the hyoid bone HB. The bend of the lever causes it to pass through the thyrohyoid membrane TM and the hyoepiglottic ligament HL.

A second end 168 of the lever 160 extends above the hyoid bone HB and projects into the interior of the tongue T. The second end 168 is secured to an anchor bolt 170 in the jawbone JB by a suture or cable 172 which is placed under tension by a surgeon. The lever 160 urges the hyoid bone forward (i.e., toward the jaw bone JB) with the advantages of the mandibular advancement or mandibular osteotomy procedures.

The lever 160 can be any suitable biocompatible material which has sufficient rigidity to act as a lever of the hyoid bone HB using the thyroid cartilage TC as a fulcrum.

Figure 20:
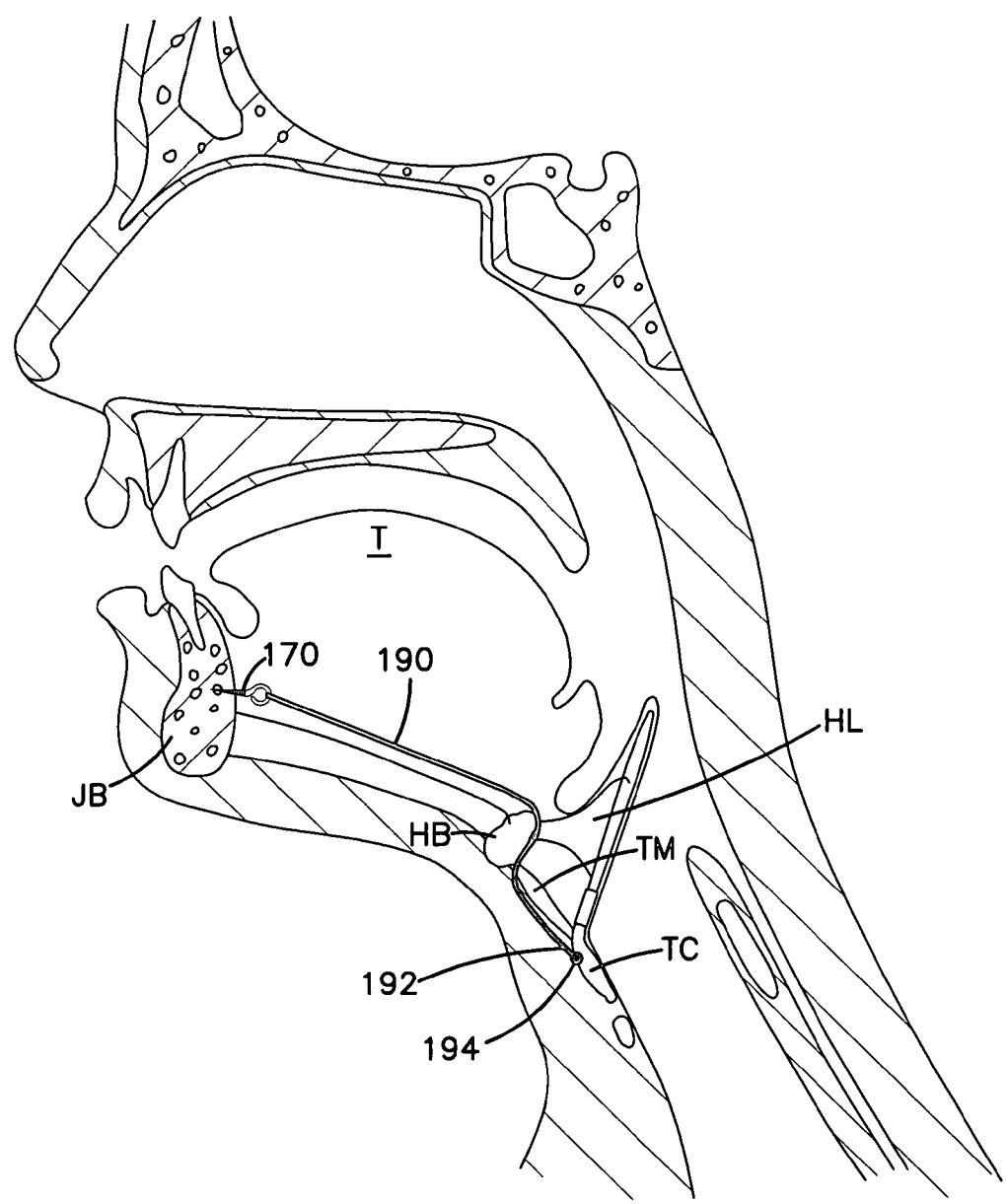
FIG. 20 is the view of FIG. 18 with the lever illustrated as a cable.

FIG. 20 illustrates a similar embodiment with a cable 190 having a first end 192 secured to the thyroid cartilage TC by sutures 194. The cable 190 is passed around the posterior side of the hyoid bone HB (and preferably secured thereto by sutures). A second end of the cable 190 is secured to the anchor 170 in the jawbone JB.

Figure 21:
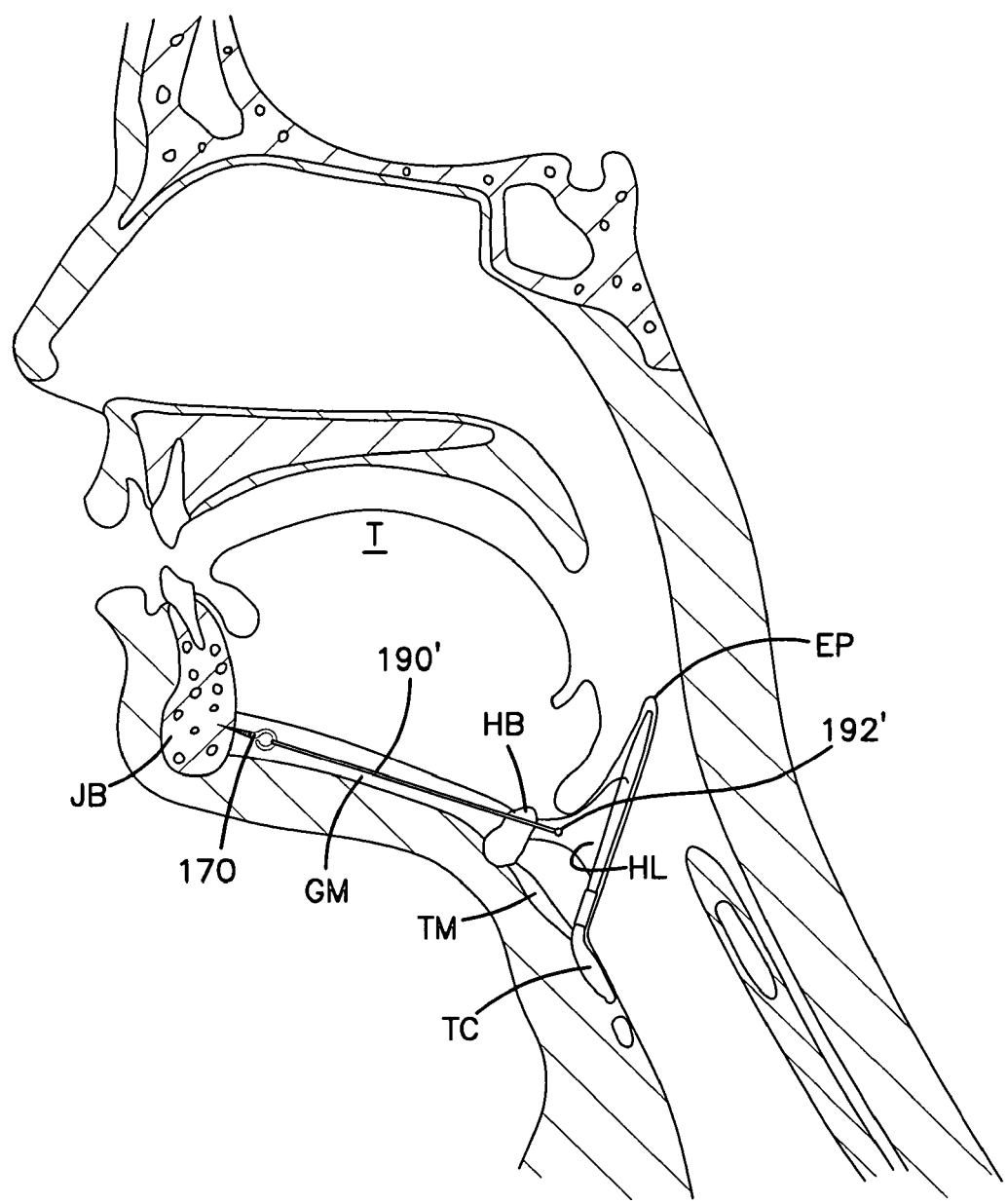
FIG. 21 is the view of FIG. 20 showing a cable secured to an epiglottis cartilage.

FIG. 21 illustrates an alternative embodiment where a cable 190' has a first end 192' secured to the hyoepiglottic ligament HL by sutures. The cable 190' passes into and is affixed to the hyoepiglottic ligament HL. The cable 190' may pass through (as shown) or over the hyoid bone HB. The cable 190' further passes through the geniohyoid muscle GM and terminates at a second end 194' at the jawbone JB where it is secured to an anchor 170.

In each of the embodiments shown in FIGS. 18, 20 and 21, in lieu of a jawbone anchor 170, a tissue embedded anchor (such as anchor 118 in FIG. 11) could be used.

B. Additional Disclosure of the Present Application

1. Tongue-Flap Formation

Referring now to FIGS. 22-30, a tool 100 is shown for forming an insertion in a tissue of a patient. More particularly, the tool 100 is suitable for forming a flap in an upper surface of a tongue of a patient. The tool 100 includes a tissue isolation member 102, an ablation member 104, and a handle 108.

Figure 29:
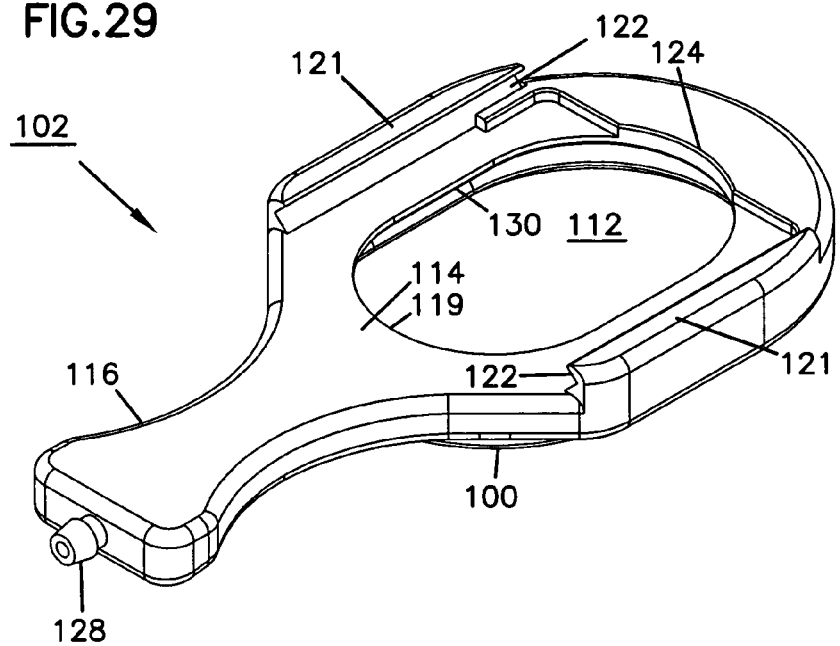
FIG. 29 is an end, top and right side perspective view of the tissue isolation member of the tool of FIG. 22.
Figure 30:
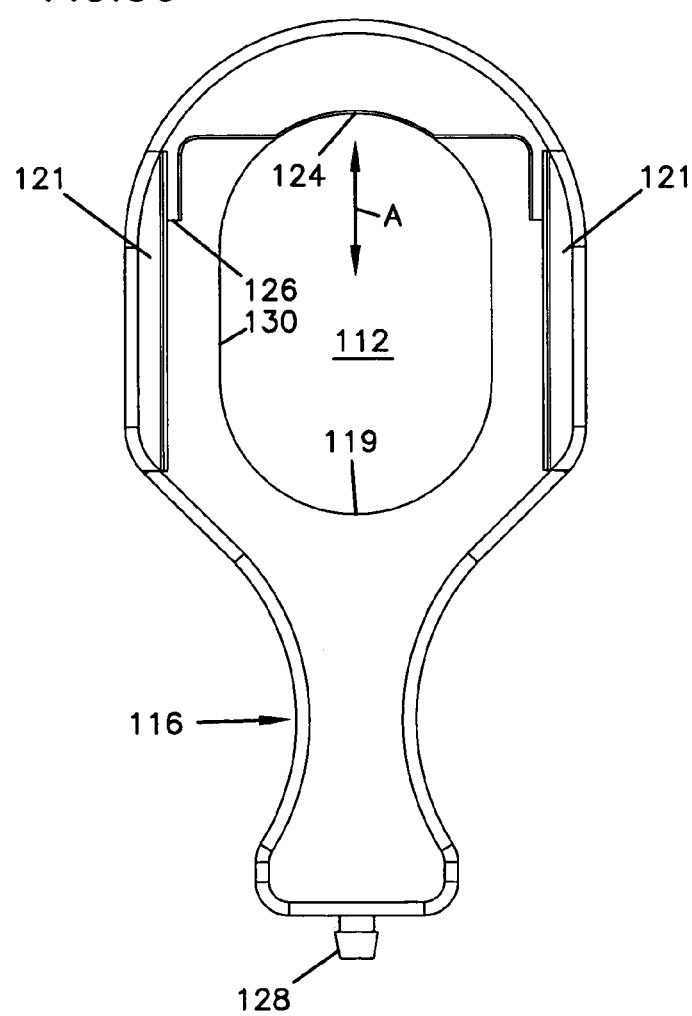
FIG. 30 is a top plan view of the tissue isolation member of FIG. 29.

The tool isolation member 102 is separately shown in FIGS. 29-30 and includes a bottom surface 110 in the form of a continuous ring to define an opening 112. The bottom surface 110 is flat for placement against a tissue of a patient. In a preferred embodiment, the bottom surface 110 is for placement against an upper surface of the tongue T. The opening 112 exposes a target tissue TT (FIG. 23), which, upon urging of the ring 110 against the tissue, is received within the opening 112.

The tissue isolation member 102 also includes a flat upper surface 114. Surface 114 is parallel to the plane of the bottom surface 110. The upper surface 114 has an extension 116 which projects away from a front side 119 of the opening 112. In the Figures, the extension 116 projects in a straight line. Alternatively, the extension may be curved downwardly. In addition to presenting less of an obstruction to a physician's line of sight, a curved extension can act as a retractor to depress a forward portion of a tongue during use of the tool 100.

Guide members 121 are carried on the tissue isolation member 102 on opposite sides of the opening 112. The guide members 121 include a tracks 122 extending in a line parallel to the bottom surface 110 and upper surface 114. The tracks 112 define an incision path represented by the arrow path A (FIG. 30) which extends across the opening 112 from the front side 119 of the opening 112 to a back side 124. A stop surface 126 is positioned on the upper surface 114 in close proximity to the back side 124 for reasons that will become apparent.

A suction conduit 127 (FIGS. 23 and 24) extends through the extension 116 and terminates at a suction port 128. The suction port 128 may be connected through a conduit (not shown) to a source of a vacuum (not shown). A wall 130 surrounds the opening 112. A groove 132 (FIGS. 23 and 24) is formed in the wall 130 with the groove 132 in airflow communication with the suction conduit 126.

The ablation member 104 includes a housing 136 (FIGS. 26-28) having a front end 138 and sidewalls 140 and bottom surface 144. The housing 136 is sized for the bottom surface 144 to slidably engage and abut the upper surface 114 of the tissue isolation member 102. When so positioned, rails 142 on the sidewalls 140 are received within the track 122 and with the guide member 121 abutting the sidewalls 140.

The front end 138 opposes the opening 112 and the ablation member 140 is slidable on the upper surface in the direction of the incision path A. The rails 142 received within the tracks 122 restrict the motion of the ablation member 104 to a back-and-forth motion in the direction of the incision path A.

The housing 142 contains a rotating shaft 146 for rotation about an axis Y-Y. A shaft 146 terminates out the rear of the housing at a shaft coupling 147 contained with a male housing coupling 148 (shown as a bayonet-style attachment). Axis Y-Y is parallel with the incision path A and centrally positioned between the sidewalls 140.

An ablation element 151 is mounted to the front end 138 of the housing 136. The ablation element 151 includes a back wall 152 parallel to the front end 138 of the housing 136. The ablation element 151 also includes a blade 154 extending substantially perpendicular away from a back wall 152 in close proximity to the bottom surface 144. The blade 154 presents a knife edge 156 which is positioned in close proximity and parallel to the bottom surface 144 and perpendicular to the incision path A. The front wall 138 is provided with a ramp 139 which angles upwardly from the knife-edge 156 toward a top wall 137 of the housing.

The back wall 152 of the blade 154 is connecting to the rotating shaft 146 by an eccentric pin 161 received within a vertical slot 163 formed in the back wall 152. The eccentric pin extends from the rotating shaft 146 parallel to but offset from the axis Y-Y. Accordingly, as shaft 146 rotates about axis Y-Y, the eccentric pin 161 translates the rotary motion of the shaft 146 to a transverse motion of the ablation element 151 such that the ablation element 151 moves in a transverse path Z-Z perpendicular to axis Y-Y and with the ablation member 151 moving in a reciprocating motion back-and-forth in the direction of path Z-Z.

The handle 108 includes a handle housing 171 for storing a battery and a motor (not shown). The handle 108 further includes a drive shaft housing 172 set at an angle relative to an axis of the handle housing 171. The drive shaft housing 172 contains a drive shaft (not shown) connected to the motor of the handle 108 by any suitable coupling to accommodate the angle between the drive shaft housing 172 and handle housing 171. It will be appreciated that motors, drive shafts and such coupling are well known in the art and form no part of this invention per se.

The drive shaft housing 172 terminates at a female coupling 174 adapted to mate with the male coupling 148. When so mated, a coupling of the drive shaft (not shown) mates with the shaft coupling 147. With the structure thus described, actuation of the motor in the handle 108 is translated to action of the ablation element 151 causing the ablation element to move back and forth in a reciprocating linear path parallel with axis Z-Z and perpendicular to incision path A.

The elements thus described are arranged such that the ablation member 104 can move in a direction of path A until the front wall 138 of the housing 136 abuts the stop 126. The stop 126 is positioned such that when the stop 126 is engaged with the front wall 138, the knife-edge 156 has moved substantially throughout the diameter of the opening 112 but has not completely traversed the opening 112.

With the construction thus described, the tool 100 is particularly suitable for forming a flap incision in a tongue of a patient. Such a procedure is illustrated in FIGS. 22-25.

As illustrated in FIGS. 22-25, the tissue isolation member 102 is placed in the patient's mouth with the bottom surface 110 opposing and abutting the upper surface of the tongue T. The angle between the handle housing 171 and drive shaft housing 172 further facilitates ease of visualization for the physician.

The physician places the tissue isolation member 102 in place on the tongue T with the opening 112 exposing a target tissue TT for creation of an incision. When so positioned, the physician may depress the tissue isolation member 102 against the tongue to cause the target tissue TT to rise within the opening 112. Further, a vacuum can be applied to the port 128 such that the vacuum is distributed to the groove 132. The vacuum in the groove 132 urges the tissue against the cylindrical wall 130 and further lifts the tissue above the upper surface 114.

With sufficient amount of tissue raised above the opening 112 and stabilized by the suction in the groove 132, the physician actuates the motor of the handle 108 to cause the blade 154 to move in a reciprocating manner along the direction Z-Z. The physician then advances the ablation member 104 relative to the isolation member 102 in the direction of arrow A.

During advancement of the ablation member 104, the knife-edge 156 slices into the tissue above the opening 112 with the resulting slice parallel to the upper surface 114. The physician continues advancement of the ablation member 104 in the direction of arrow A with the partially severed tissue flap F lifted by the ramp 139.

Incision formation is continued until the front wall 138 abuts the stop 126. At this point, the knife-edge 156 has not completely passed over the opening 112. Therefore, the flap F of tissue is not completely severed from the tongue T. As a result of the procedure, the physician has formed flap F and defined a pocket P beneath the upper surface of the tongue T.

Upon achieving the stop 126, the physician turns off the motor, retracts the ablation member 104 relative to the tissue isolation member 102 and removes the assembled tool 100 from the patient. The tissue isolation member 102 and ablation member 104 may conveniently be formed as disposable members avoiding the need for re-sterilization. The handle 108 may be a reusable member for use in later procedures.

The materials of the tissue isolation member 102 and ablation member 104 may be made of plastic or other members or materials of sufficient rigidity to withstand the forces of the operation as well as the rigors of sterilization. Preferably, the ablation element 151 is formed of surgical steel or other metals sufficient to form and retain a sharp knife-edge 156 as well as withstand the rigors of sterilization.

2. Tongue Muscle Compression i. First Disclosed Embodiment

FIGS. 31-36 illustrate an implant system 210 for compressing a muscle group of a tongue T of a patient and of forming the tongue T in such a manner to treat obstructive sleep apnea. The apparatus 210 includes a first or outer brace 212 and a second or lower brace 212'.

The braces 212 and 212' have substantially identically shaped body portions 214, 214'. It will appreciate that a discussion of the body portion 214 will suffice as a discussion of body portion 214' since they are identical and numbered identically with the addition of an apostrophe to distinguish the outer and lower body portions 214, 214'.

The body portions 214, 214' have a length L, width W and thickness TH. The length L extends between the ends 215, 215a. The width W extends transversely to the length L between sides 216, 216a and the thickness T extends between outer and inner surfaces 217, 217a.

Centrally positioned on the inner surface 217a of body portion 214 is a hub 218 which is provided with an internal threaded bore 220 having axis X-X perpendicular to the plane of surface 217a. Centrally positioned on body portion 214' is a bore 220' extending completely through the wall thickness T of the body portion 214'. At the outer surface 217', the bore 220' is countersunk.

On opposite sides of the hub 218 and the bore 220', each of the body portions 214, 214' has two holes 221, 221a extending through the wall thickness T. The holes 221, 221a are generally oval in shape and each has a major axis Y-Y extending substantially from the hub 218 to the ends 215, 215a and a minor axis Z-Z extending substantially between the side edges 216, 216a.

The ends 215, 215a are rounded to present a blunt surface. Further, the ends 215, 215a are radiused toward the inner surface 217a and recessed beneath the inner surface 217a by a depth D.

A connecting element 230 is provided in the form of a rigid rod having a threaded first end 232 adapted to be threadedly engaged with the threaded bore 220 of hub 218. A second end 234 is sized to be received within the countersunk hole 220' such that end 234 of the connecting element 230 is flush with surface 217'. The ends 232, 234 are connected by a hollow shaft 236 having a plurality of holes 238 formed through the wall of the shaft 236 into communication with the interior of the hollow shaft 236.

With the construction thus described, the braces 212, 212' can be aligned with inner surfaces 217a, 217a' in opposition. The threaded end 232 is passed through bore 220' and threadedly engaged with bore 220. The end 234 is received within the countersunk hole 220'.

So connected, the shaft 236 defines a spacing S (FIG. 31) between the surfaces 217a and 217a'. The spacing S can be adjusted by continuing the threading of the end 232 within the bore 220 to adjust the spacing S. With this combination, the hub 218 cooperates with element 230 for the element 230 to have an adjustable length representing an adjustment of the spacing between the braces 212, 212'. The end 234 is provided with a shaped recess 237 (FIG. 36) to receive the tip of any suitable complimentarily shaped tool (not shown) to turn the element 230.

Figure 31:
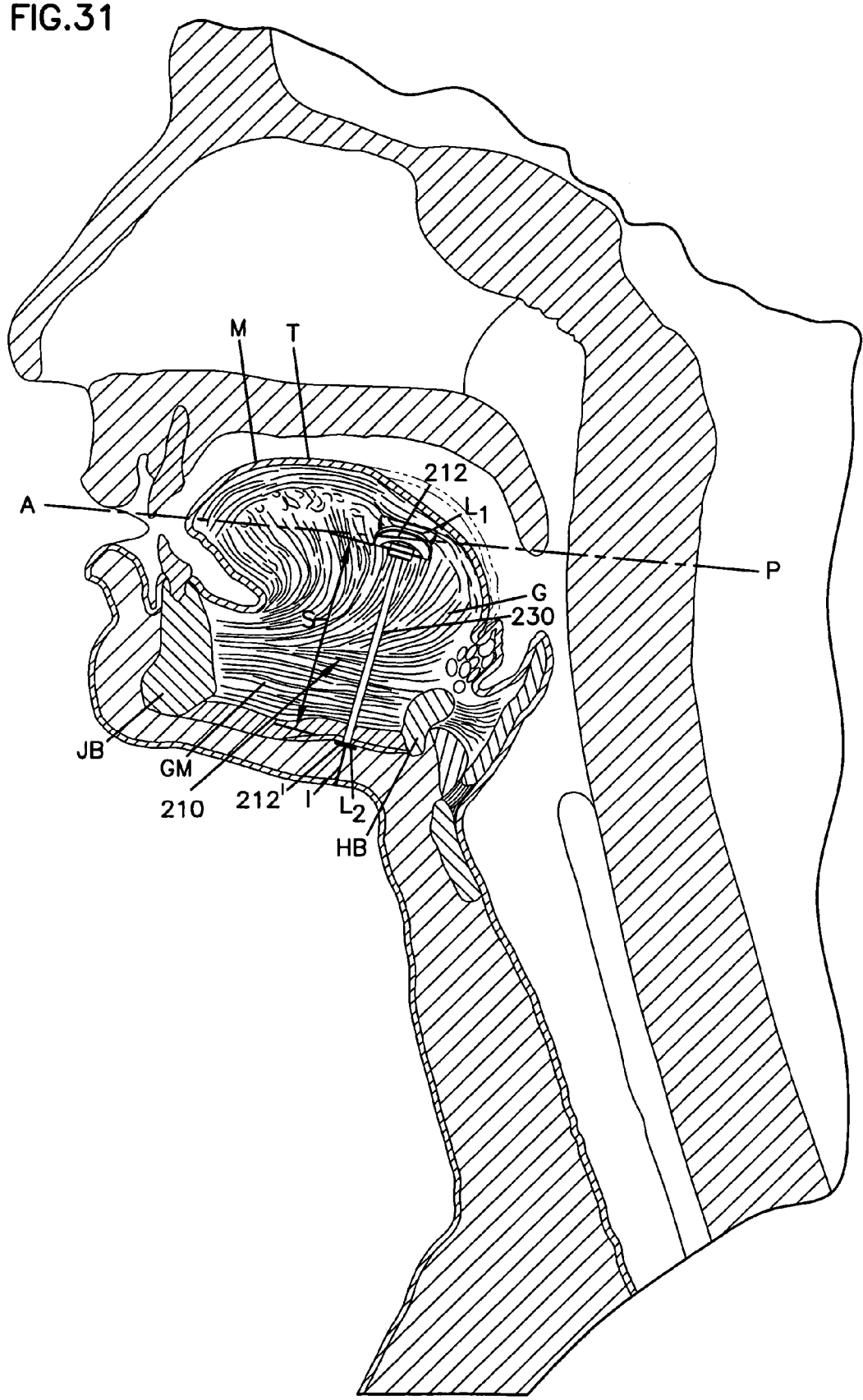
FIG. 31 is a view similar to that of FIG. 22 and showing a muscle compression apparatus according to the present invention in the tongue.
Figure 37:
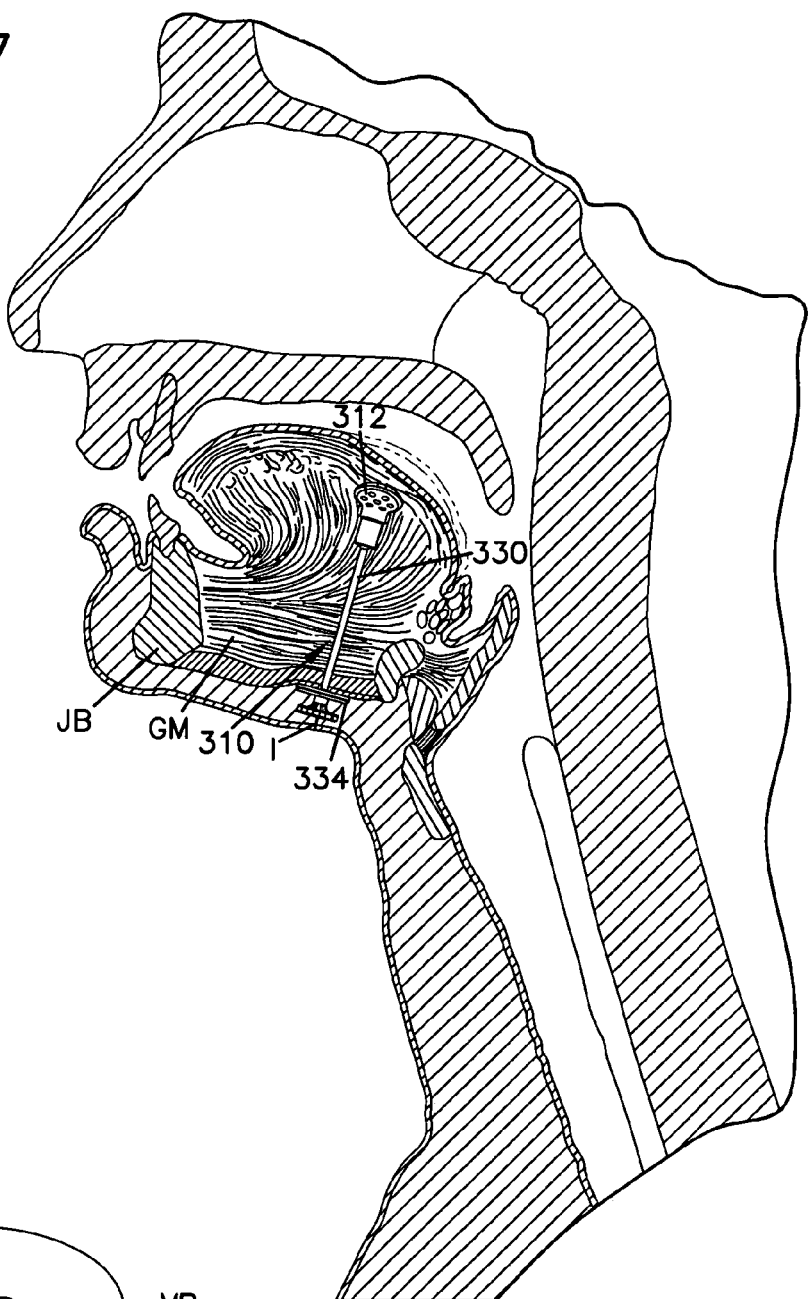
FIG. 37 is a view similar to that of FIG. 22 and showing a muscle compression apparatus according to an alternative embodiment of the present invention in the tongue.

FIG. 31 illustrates the apparatus 210 in a desired position within a tongue T of a patient. As shown in the figures, a first implant location $L_1$ is identified in the genioglossus muscle G beneath the mucosal layer M of the tongue T. Preferably, this location $L_1$ is positioned as rearward as possible on the tongue but, preferably, not in lymph tissue. Also, location $L_1$ is preferably about 1-3 cm beneath the mucosa M. A second implant location $L_2$ is identified spaced beneath the first implant location $L_1$. Preferably, this location $L_2$ is positioned beneath a lower muscle layer beneath the geniohyoid muscle GM. Alternatively, this location could be between the genioglossus G and the geniohyoid muscle GM.

The first brace 212 is placed at the first implant location $L_1$ with a surface 217a facing downwardly toward the genioglossus muscle G. The second brace 212' is received at the second implant location $L_2$ with the surface 217a' facing upwardly toward the genioglossus muscle G. The connecting element 230 is received between the braces 212, 212' with turning of the connecting element 230 drawing the braces 212, 212' towards one another to compress the genioglossus muscle G.

The downwardly curved ends 215, 215a are urged into the opposing muscle relative to the plane of surfaces 217a, 217a' and resist lateral movement of the braces 212, 212' following implantation. The blunt edges of the braces 212, 212' prevent injury to the muscle. Further, tissue of the muscle and the tongue can pass through and grow through the openings 21, 21a' as well as grow through the holes 238 of the shaft 236 such that the device 210 is firmly captured within the tongue and restricted from relative movement following implantation.

Figure 22:
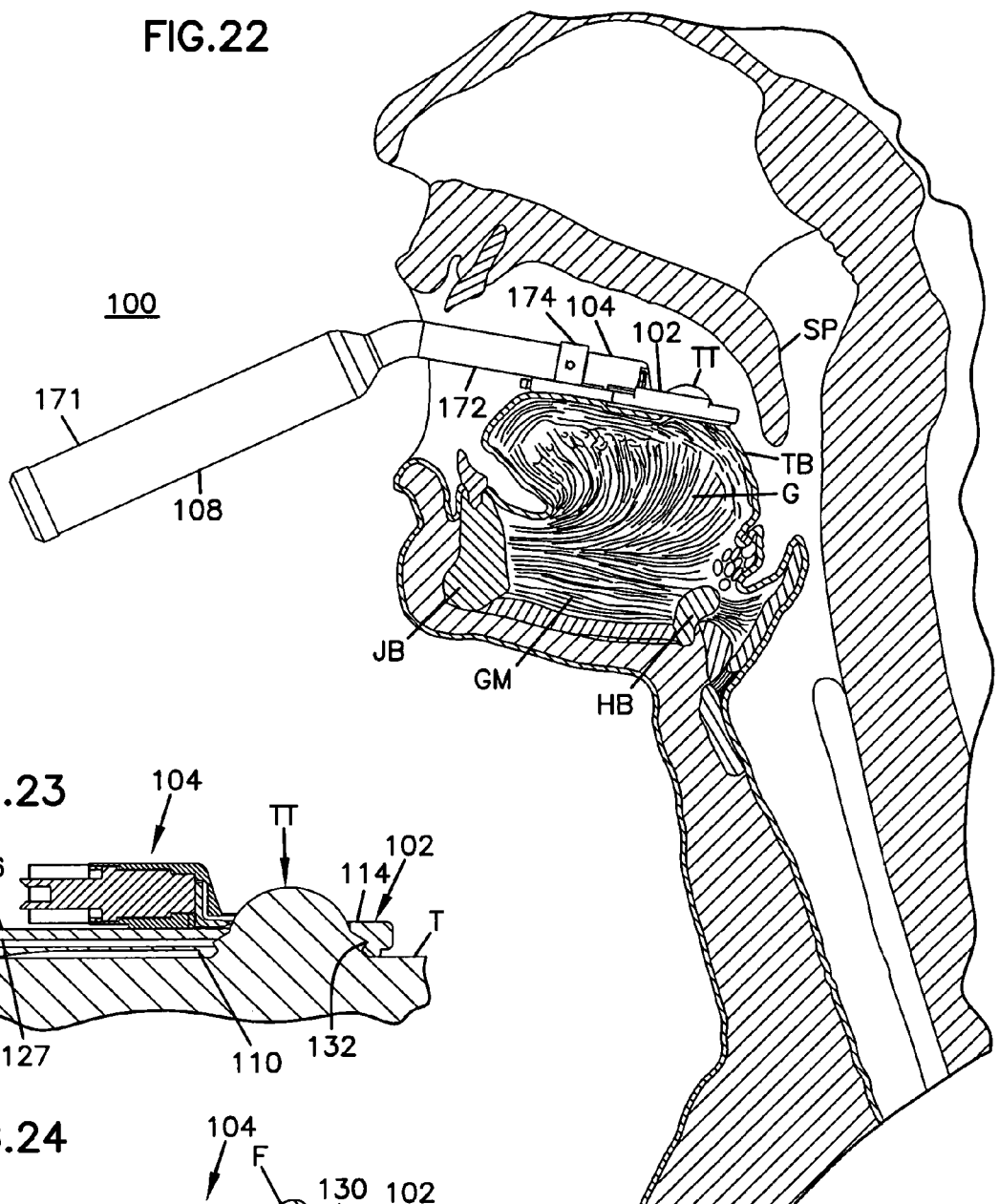
FIG. 22 is a view similar to that of FIG. 1 and showing a tool according to the present invention for forming a flap incision in the tongue.
Figure 23:
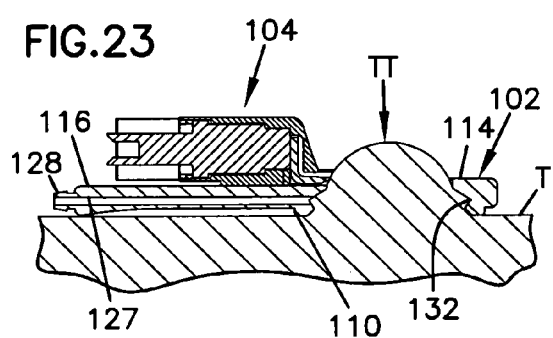
FIG. 23 is a side sectional view of the distal end of tool of FIG. 22 initiating an incision formation.
Figure 24:
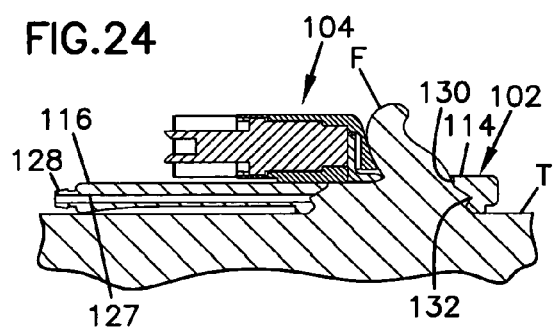
FIG. 24 is the view of FIG. 23 showing partial formation of a flap incision.
Figure 25:
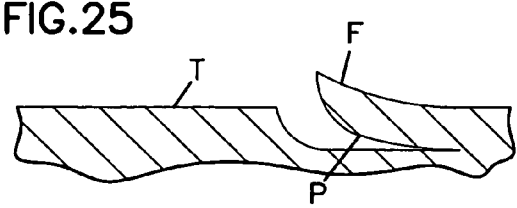
FIG. 25 is the view of FIG. 24 following complete formation of a flap.
Figure 26:
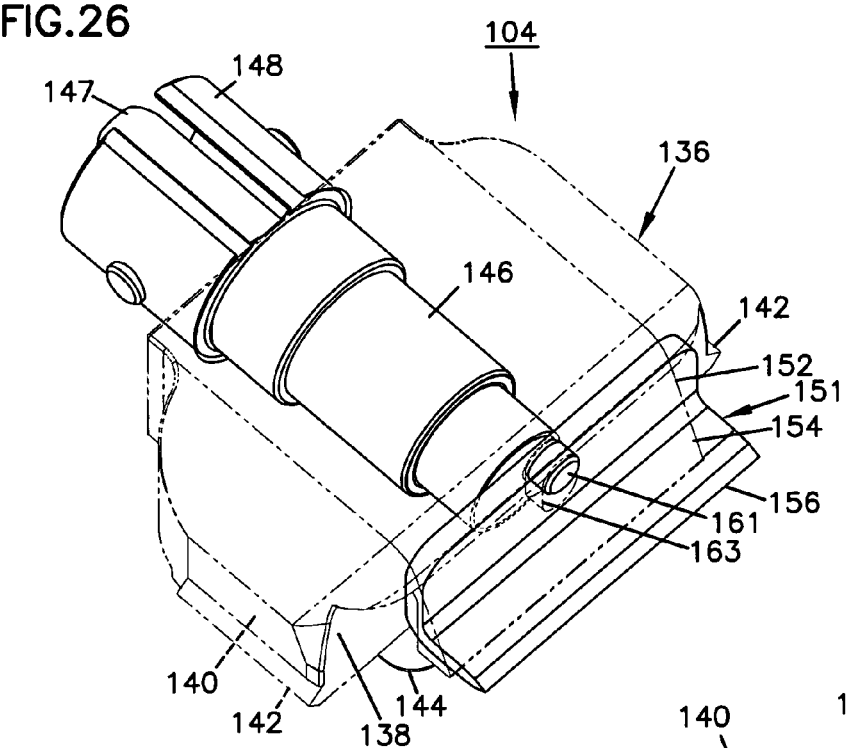
FIG. 26 is an end, top and right side perspective view of the distal end of the tool of FIG. 22.
Figure 27:
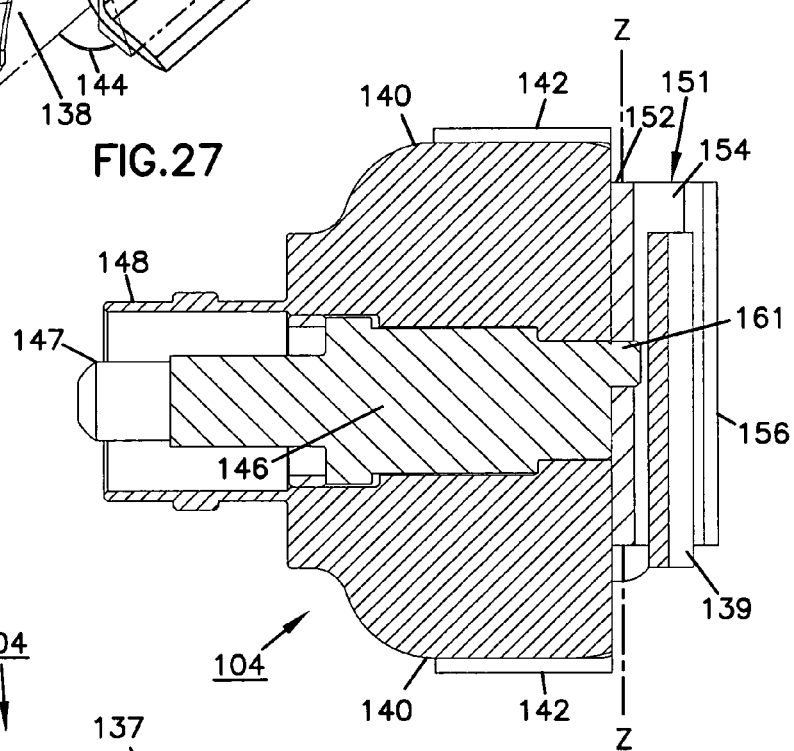
FIG. 27 is a top sectional view of the tool of FIG. 26.
Figure 28:
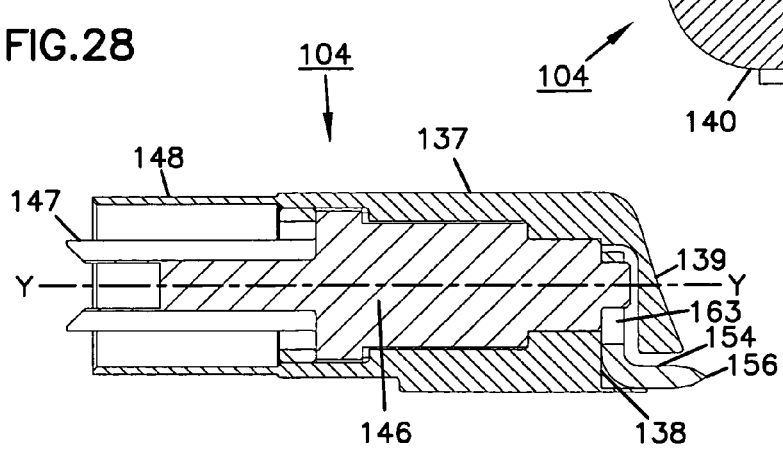
FIG. 28 is a top sectional view of the tool of FIG. 26.

To implant the device 210, a flap is formed in the tongue T near the base of the tongue using the tool 100 of FIG. 22. The first brace 212 is positioned beneath the flap with the upper surface 217 opposing the top of the tongue T and with the lower surface 217a facing toward the chin of the patient.

It will be appreciated that the flap formed by the tool need not be sized to completely pass the first brace 212 into the pocket. Instead, the flap can provide an opening into the interior tissue of the tongue. Within the pocket, the brace 212 is oriented such that its longitudinal axis L is transverse to the anterior-posterior axis A-P of the patient and, with the width W substantially in line with anterior-posterior axis. While such a positioning is preferred, the longitudinal axis L could be placed parallel to the anterior-posterior axis A-P.

To place the second brace 212', an incision I is made beneath the chin of the patient anterior to the hyoid bone HB to define a surgically created path from the incision to the second implant location $L_2$. The second brace is 212' is oriented in the same manner as the first brace 212. The braces 212, 212' are then connected by passing the end 232 of the connecting element 230 through the hole 220' and into threaded engagement with the hub bore 220.

Figure 44:
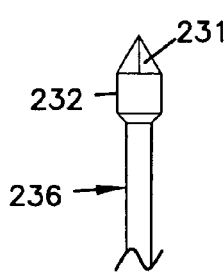
FIG. 44 is a side elevation view of a first end of a connecting element showing an alternative embodiment equipped with a tissue penetrating tip.
Figure 45:
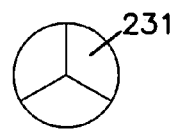
FIG. 45 is an end view of the tip of FIG. 44.

To facilitate the passage, an incision path can be formed between the braces 212, 212'. Alternatively, the first end 230 can be provided with a sharp tissue-penetrating tip 231 as illustrated in FIGS. 44-45. The tip 231 has three flats terminating at a sharp tip 231. The edges of the flats are cutting edges. Upon coupling of the end 230 to hub 218, the sharp tip 231 is enclosed within the hub 218 avoiding further trauma to tissue.

The spacing S of the braces 212, 212' can be adjusted by the physician turning the head 234 of the shaft 236 thus adjusting the length of the connecting element 230 by further receiving the head 232 into the hub 218. Accordingly, an amount of compression on the genioglossus muscle G (and geniohyoid muscle GM) can be adjusted by the surgeon. As little as 2 mm of compression may be adequate for a positive therapeutic effect. Compression of the genioglossus muscle with the aforementioned device 210 reshapes the tongue T and resists its collapse against the pharyngeal wall during sleep to maintain the airway patent during sleep. It will be appreciated that in the figures, the compression and re-shaping of the tongue T are shown exaggerated for ease of illustration.

The apparatus 210 can be formed of any suitable materials to resist the forces of placement in the tongue and may be rigid plastic or metal such as stainless steel or the like. The braces 212, 212' and connecting element 230 may also be provided with surface treatments (such as surface porosity or coatings) to promote fibrosis attachment to the tissue of the tongue. Alternatively, the braces 212, 212' and connecting element 230 may be surface treated to prevent such fibrosis to permit easy removal of the device 210 at a later date if so desired.

The device 210 may be fabricated of materials or be provided with material sites of radiopaque material to permit visualization and identification in x-rays or the like post-implantation. Numerous sizes may be provided for different sized tongues T or muscle groups (for example, the braces 212, 212' may be placed at upper and lower planes of the geniohyoid muscle GM.

ii. Second Disclosed Embodiment

FIGS. 37-43 illustrate an alternative embodiment implant system 310 for compressing a muscle group of a tongue T of a patient and for forming the tongue T in a manner to treat obstructive sleep apnea. The apparatus 310 includes a brace 312 having a body portion 314. The body portion 314 has a length L, width W, and thickness TH. The length L extends between ends 315, 315a. The width W extends transversely between sides 316, 316a transverse to the length L. The thickness T extends between outer and inner surfaces 317, 317a.

A hub 318 projects away from surface 317a and perpendicular thereto with the hub 318 positioned centrally along the length L. The hub 318 includes a threaded bore 320 with its axis X-X perpendicular to the surface 317a.

The body portion 314 is concave upwardly relative to the hub 318. The ends 315 include holes 321, 321a extending through the thickness TH of the body portion 314. The ends 315, 315a are rounded. Also, side edges 316, 316a are rounded to present an atraumatic surfaces free of sharp edges.

A connecting element 330 is provided in the form of a rigid rod 331 having a threaded first end 332 adapted to be threadedly engaged within the threaded bore 320 of hub 318. A second end 334 is provided with a head 336 which is configured to be engaged by an operator to turn the head 336 to thereby turn shaft 331 and threaded end 332. It will be appreciated that in lieu of the knobbed head 336 any other head configuration could be employed. For example, the head 336 could be provided with a slot to receive a turning tool such as a driver or the like to engage the head and cause rotation of the head about the axis of the rod 331.

A flange 338 is secured to the rod 331 adjacent head 336. The flange 338 is sized to resist displacement of the flange 338 through opposing tissue. The surface area 317a is also sized to resist displacement of the body portion 314 through opposing tissue.

Figure 38:
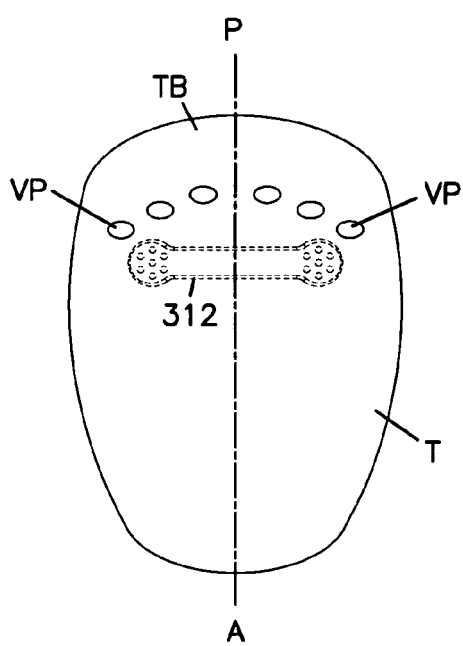
FIG. 38 is a top plan view of the tongue showing, in phantom lines, a brace member of the apparatus of FIG. 37.
Figure 39:
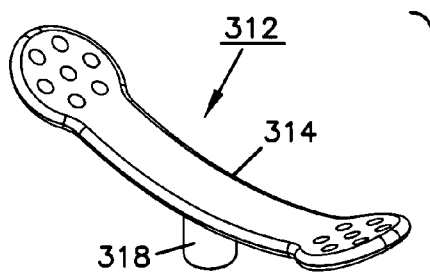
FIG. 39 is a top, front and end, exploded perspective view of the muscle compression apparatus of FIG. 37.
Figure 40:
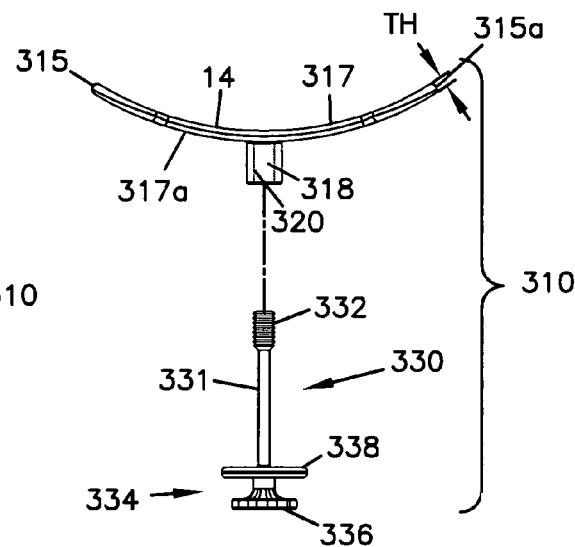
FIG. 40 is a front elevation exploded view of the muscle compression apparatus of FIG. 39.
Figure 42:
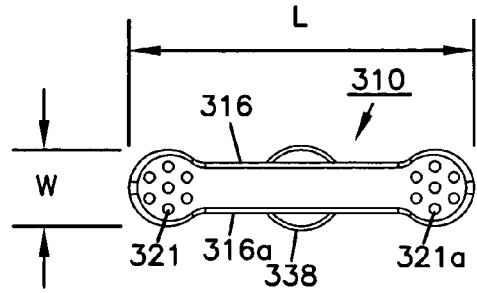
FIG. 42 is a top plan view of the muscle compression apparatus of FIG. 39.
Figure 41:
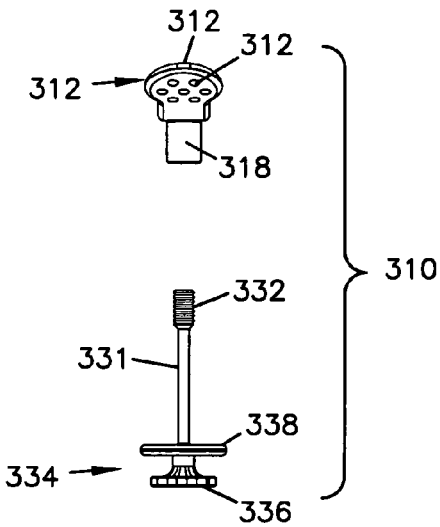
FIG. 41 is an end elevation exploded view of the muscle compression apparatus of FIG. 39.
Figure 43:
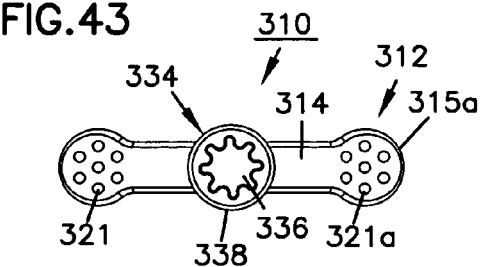
FIG. 43 is a bottom plan view of the muscle compression apparatus of FIG. 39.

With the construction thus described, a flap is formed in the tongue T near the base of the tongue using the tool 100 of FIG. 22. The body portion 314 is positioned beneath the flap with the concave upper surface 317 opposing the top of the tongue and with the body surface 317a facing toward the chin of the patient. FIG. 38 shows the brace 312 implanted in the tongue T just anterior to vallate papillae.

It will be appreciated that the flap formed by the tool need not be sized to completely pass the body portion 314 and brace 312 into the pocket. Instead, the flap can provide an opening into the interior tissue of the tongue. The surgeon can then place the brace 312 within the tongue using the ends 315, 315a as blunt dissection tools to form and enlarge the pocket to receive the brace 312. Within the pocket, the brace 312 is oriented such that its longitudinal axis L is transverse to the anterior-posterior axis A-P of the patient and with the width W substantially in line with anterior-posterior axis.

An incision I is formed beneath the chin of the patient and anterior to the hyoid HB to define a surgically created path from the incision to the hub 318. The connecting member 330 is passed through the incision path by aligning the axis of the rod 331 with the incision path and inserting the threaded end 332 into the incision path and moving the connecting element 330 until the threaded end 332 threadedly engages the hub 318. As in the previous embodiment, instead of forming an incision all the way to the hub 318, an incision can be made through the skin of the chin and a sharp-tipped connecting member can be passed through to the hub 318.

In a preferred embodiment, the connecting element 330 is sized for the threaded end 32 to engage the hub 318 with the flange 338 opposing the bottom of the geniohyoid muscle GM of the patient. At such position, the flange 338 is opposing the geniohyoid muscle GM and the head 338 is fully received and implanted within the patient.

Prior to closing the incision, the surgeon can adjust the spacing between the flange 338 and the brace 312 by drawing and rotating the connecting element 330 to further insert the threaded end 332 within the hub 320. The incision can then be closed. Such action draws the base of the tongue away from the pharyngeal wall and the roof of the mouth with the flange 338 opposing the geniohyoid muscle preventing migration of the connecting element into the tongue. In the present embodiment as well as the previously disclosed embodiment, the physician can re-adjust the spacing S at a later date if so desired.

The connecting element 330 is formed of any suitable material to resist elongation. The device may be provided with material sites of radiopaque material to permit visualization and identification in x-rays or the like post-implantation. The apparatus can be formed with any suitable materials to resist the forces of placement in the tongue, and may be rigid plastic or metal such as stainless steel or the like. Surfaces of the components of the apparatus may be provided with surface treatments (such as surface porosity or coatings) to promote fibrosis attachment to the tissue of the tongue. Further, tongue tissue may grow into the holes 320 to prevent displacement of the tongue and displacement of the device within the tongue. Alternatively, components may be surface treated to prevent such fibrosis to permit easier removal of the device at a later date if so desired.

Figure 46:
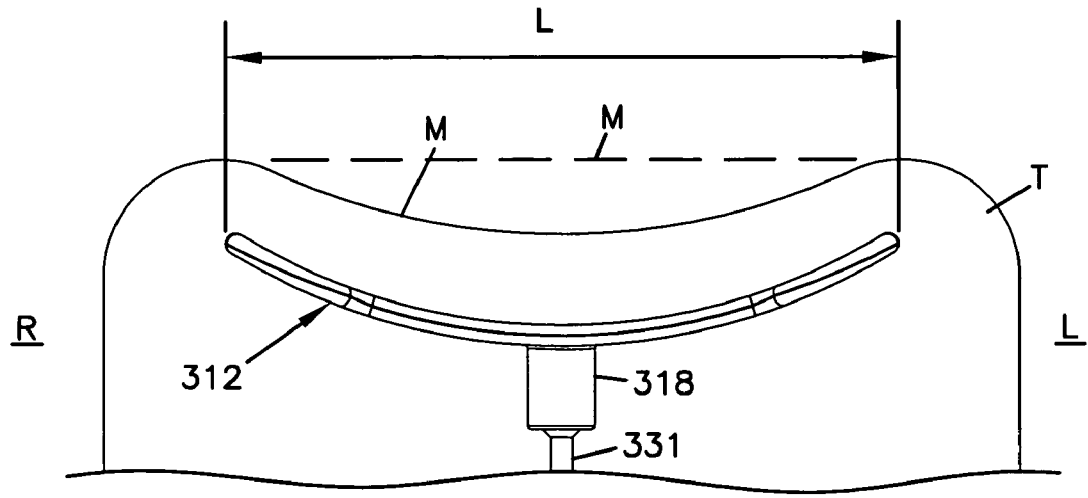
FIG. 46 is a sectional view taken perpendicular to an anterior-posterior axis of the tongue showing a resulting compression of a first sized apparatus according to the present invention.
Figure 47:
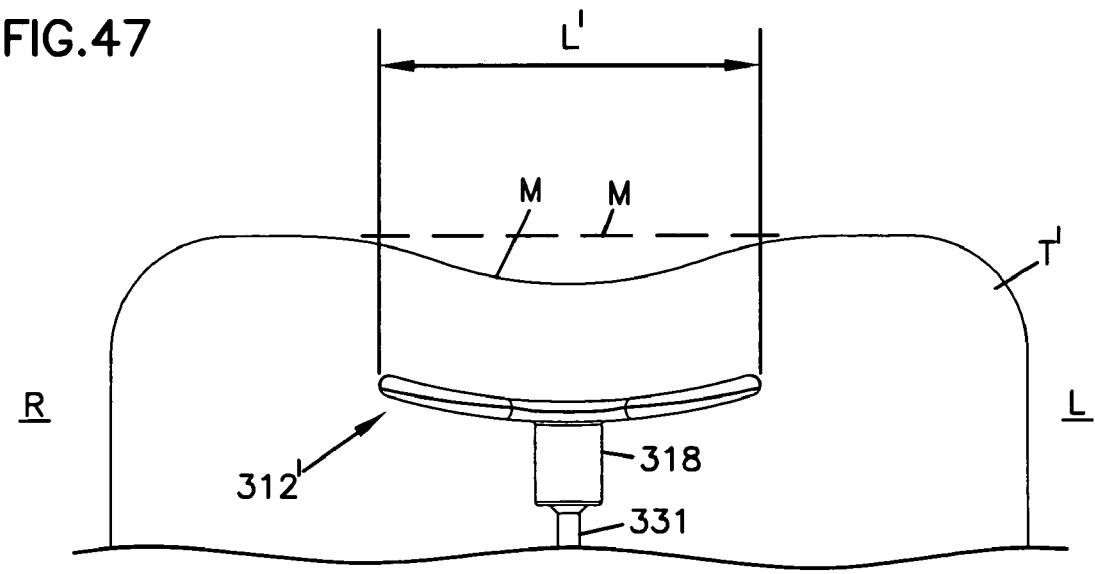
FIG. 47 is the view of FIG. 46 showing a resulting compression of a second sized apparatus according to the present invention.

FIGS. 46 and 47 illustrates how the brace 312 both compresses the tongue T and re-shapes the tongue T. It will be appreciated that this discussion also applies to the previously described embodiment. The original mucosal surface M is shown pre-treatment in phantom lines and post-treatment in solid lines. The view of FIGS. 46 and 47 is a section taken perpendicular to the anterior-posterior axis and showing the left L and Right R sides (from the patient's perspective).

As the brace 312 is retracted toward the chin, the mucosa M re-shapes. The amount of re-shaping is more pronounced in the center of the tongue T. FIG. 47 illustrates how the re-shaping can be focused in the center of the tongue with a brace 312' of shorter length L'.

The surface size of both braces 312, 312' (as well as braces 212, 212') resist migration through the tissue of the tongue T. The flat inner surfaces (217a, 217a', 317a) oppose tissue and prevent migration in response to compression forces. Only blunt edges oppose tissue to avoid slicing through tissue.

The foregoing describes numerous embodiments of an invention for an implant for the tongue to treat obstructive sleep apnea or other airway conditions. Having described the invention, alternatives and embodiments may occur to one of skill in the art. For example, instead of a rigid shaft 331, 236, the shafts may be replaced with a cable which resists elongation but is otherwise flexible. It is intended that such modifications and equivalents shall be included within the scope of the following claims.

What is claimed is:

1. A method for treating an upper airway condition, said method including:
   identifying a patient with obstructive sleep apnea;
   identifying a muscle of a tongue of said patient;
   implanting a first brace within said tongue at a first implant location at an upper location in said muscle;
   implanting a second brace within said tongue at a second implant location spaced below said upper location;
   connecting said first and second braces to resist an elongation of a spacing between first and second braces;
   wherein said first brace is a plate having a length, width and thickness with said thickness substantially less than either of said length and width, and wherein said method further including:
   implanting said first brace in a first implant orientation with said length substantially transverse to an anterior-posterior axis of said tongue and with said width substantially in-line with said axis.

2. A method for treating an upper airway condition, said method including:
   identifying a patient with obstructive sleep apnea;
   identifying a muscle of a tongue of said patient;
   implanting a first brace within said tongue at a first implant location at an upper location in said muscle;
   surgically accessing said first implant location by an incision through a mucosal layer said tongue and
   placing said first brace in said first implant location and in said alignment beneath said mucosal layer
   implanting a second brace within said tongue at a second implant location spaced below said upper location;
   connecting said first and second braces to resist an elongation of a spacing between first and second braces;
   wherein said muscle includes a genioglossus muscle.

3. A method according to claim 2 wherein said surgical access includes formation of a mucosal flap and placing said first brace beneath said flap.

4. A method for treating an upper airway condition, said method including:
   identifying a patient with obstructive sleep apnea;
   identifying a muscle of a tongue of said patient;
   implanting a first brace within said tongue at a first implant location at an upper location in said muscle;
   implanting a second brace within said tongue at a second implant location spaced below said upper location;
   connecting said first and second braces to resist an elongation of a spacing between first and second braces;
   wherein said second brace is a plate having a length, width and thickness with said thickness substantially less than either of said length and width, and wherein said method further including:
   implanting said second brace in a second implant orientation with said length substantially transverse to an anterior-posterior axis of said tongue and with said width substantially in-line with said axis.

5. A method according to claim 4 further comprising:
   surgically accessing said second implant location by an incision beneath a chin of said patient; and
   placing said second brace in said second implant location and in said alignment beneath said mucosal layer.

6. A method for treating an upper airway condition, said method including:
   identifying a patient with obstructive sleep apnea;
   forming an upper incision through an upper surface of a tongue of said patient to define a pocket to receive an implant;
   selecting a brace member sized to be received within said pocket, said brace member having a lower surface opposing tissue of said tongue;
   inserting said brace member into said pocket;
   closing said upper incision;
   inserting a retaining member through a bottom of said tongue and coupling a first end of said retaining member to said brace member; and
   securing a second end of said retaining member to tissue in proximity to said bottom of said tongue;
   wherein said brace member is a plate having a length, width and thickness with said thickness substantially less than either of said length and width, said method including:
   inserting said brace member in said pocket with an orientation for said length to be substantially transverse to an anterior-posterior axis of said tongue and with said width substantially in-line with said axis.

7. A method according to claim 6 wherein said retaining member includes a longitudinal axis, said inserting of said retaining member includes:
   surgically accessing said pocket by a lower incision beneath a chin of said patient and through said bottom of said tongue and defining a surgically created path from said lower incision to said pocket;
   orienting said retaining member with said longitudinal axis substantially aligned with said surgical path;
   advancing said retaining member in said alignment through said surgically created path to said pocket;
   securing said first end to said first brace.

8. A method for treating an upper airway condition, said method including:
   identifying a patient with obstructive sleep apnea;
   forming an upper incision through an upper surface of a tongue of said patient to define a pocket to receive an implant;
   selecting a brace member sized to be received within said pocket, said brace member having a lower surface opposing tissue of said tongue;
   inserting said brace member into said pocket;
   closing said upper incision;
   inserting a retaining member through a bottom of said tongue and coupling a first end of said retaining member to said brace member; and
   securing a second end of said retaining member to tissue in proximity to said bottom of said tongue;
   wherein said retaining member includes an elongated member terminating at said first end and adapted to be coupled to said brace member, said retaining member further including retention plate at said second end, said securing of said second end including implanting said second end near said bottom of said tongue with said plate resisting migration of said second end toward said upper surface of said tongue.

9. An apparatus for treating obstructive sleep apnea of a patient, said apparatus including:
   a first brace dimensioned so as to be implanted at a first implant location within a muscle of a tongue of said patient below a mucosal layer of said tongue;
   a retaining member dimensioned so as to be implanted within said tongue at a second implant location below said first implant location; and
   a connecting element adapted to connect said first brace and said retaining member to resist an elongation of a spacing between first brace and said retaining member;

said first brace is a plate having a length, width and thickness with said thickness substantially less than either of said length and width;

said length, width and thickness sized for said first brace to be implanting in a first implant orientation with said length substantially transverse to an anterior-posterior axis of said tongue and with said width substantially in-line with said axis.

10. An apparatus for treating obstructive sleep apnea of a patient, said apparatus including:

a first brace dimensioned so as to be implanted at a first implant location within a muscle of a tongue of said patient below a mucosal layer of said tongue;

a retaining member dimensioned so as to be implanted within said tongue at a second implant location below said first implant location; and a connecting element adapted to connect said first brace and said retaining member to resist an elongation of a spacing between first brace and said retaining member;

said retaining member is a plate having a length, width and thickness with said thickness substantially less than either of said length and width;

said length, width and thickness sized for said retaining member to be implanting in a second implant orientation with said length substantially transverse to an anterior-posterior axis of said tongue and with said width substantially in-line with said axis.

11. An apparatus according to claim 10 wherein said connecting element is adapted to resist elongation.

12. An apparatus according to claim 11 wherein said connecting element has an adjustable length.

13. An apparatus according to claim 11 wherein said connecting element is rigid.

* * * * *